US011100914B1

(12) United States Patent

Perahia et al.

(10) Patent No.: US 11,100,914 B1

(45) Date of Patent: Aug. 24, 2021

(54) PHONONIC CRYSTAL COUPLER

(71) Applicant: HRL Laboratories, LLC, Malibu, CA (US)

(72) Inventors: Raviv Perahia, Agoura Hills, CA (US); Jeremy Bregman, Malibu, CA (US); Amit M. Patel, Santa Monica, CA (US); Sean M. Meenehan, Malibu, CA (US); Logan D. Sorenson, Malibu, CA (US); Lian X. Huang, Malibu, CA (US)

(73) Assignee: HRL Laboratories, LLC, Malibu, CA (US)

( * ) Notice: Subject to any disclaimer, the term of this patent is extended or adjusted under 35 U.S.C. 154(b) by 393 days.

(21) Appl. No.: 16/258,271

(22) Filed: Jan. 25, 2019

Related U.S. Application Data

(60) Provisional application No. 62/622,752, filed on Jan. 26, 2018.

(51) Int. Cl.
*G10K 11/00* (2006.01)
*G10K 11/18* (2006.01)
*A61F 11/06* (2006.01)

(52) U.S. Cl.
CPC ...... *G10K 11/18* (2013.01); *G10K 2210/3214* (2013.01)

(58) Field of Classification Search
CPC ...................... G10K 11/18; G10K 2210/3214
USPC ....................................... 381/71.14; 181/175
See application file for complete search history.

(56) References Cited

U.S. PATENT DOCUMENTS

| | | | | |
|---|---|---|---|---|
| 8,054,145 B2 | 11/2011 | Mohammadi et al. | | |
| 10,281,277 B1 | 5/2019 | Perahia et al. | | |
| 2009/0295505 A1 | 12/2009 | Mohammadi et al. | | |
| 2013/0255906 A1 | 10/2013 | Chang et al. | | |
| 2015/0237423 A1* | 8/2015 | Bahr | H04R 1/00 | 381/162 |

FOREIGN PATENT DOCUMENTS

| | | |
|---|---|---|
| JP | 2014-166610 A | 9/2014 |

OTHER PUBLICATIONS

Boucher, P. et al., "Ring waveguides for gigahertz acoustic waves on silicon", Applied Physics Letters, 2014, pp. 161904-1 through 161904-4, vol. 105, AIP Publishing LLC.

(Continued)

*Primary Examiner* — Ammar T Hamid

(74) *Attorney, Agent, or Firm* — Lewis Roca Rothgerber Christie, LLP

(57) ABSTRACT

A phononic coupler. In some embodiments, the phononic coupler includes a sheet, including a plurality of standard reflectors, and a plurality of divergent reflectors. The divergent reflectors define, among the standard reflectors, a first waveguide, and a second waveguide. The coupler has a first port, at a first end of the coupler, a second port, at the first end of the coupler, and a third port, at a second end of the coupler. The first waveguide has a first end at the first port. The second waveguide has a first end at the second port, and a second end at the third port. The coupler is configured to couple longitudinal sound waves to both the first port and the second port.

21 Claims, 31 Drawing Sheets

(56) References Cited

OTHER PUBLICATIONS

Cicek, Ahmet et al., "Evanescent coupling between surface and linear-defect guided modes in phononic crystals", Journal of Physics D: Applied Physics, 2016, pp. 1-8, vol. 49, IOP Publishing Ltd.
Cicek, Ahmet et al., "Phononic crystal surface mode coupling and its use in acoustic Doppler velocimetry", Ultrasonics, Oct. 23, 2015, pp. 78-86, vol. 65, Elsevier B.V.
Hatanaka, D. et al., "Phononic crystal waveguides for electromechanical circuits", Jan. 22, 2014, pp. 1-12, arXiv:1401.5573v1.
He, Zhaojian et al., "Guiding acoustic waves with graded phononic crystals", Solid State Communications, Jul. 12, 2008, pp. 74-77, vol. 148, Elsevier Ltd.
Khelif, A. et al., "Guiding and bending of acoustic waves in highly confined phononic crystal waveguides", Applied Physics Letters, May 31, 2004, pp. 4400-4402, vol. 84, No. 22, American Institute of Physics.
Lin, SZ-Chin Steven et al., "Acoustic mirage in two-dimensional gradient-index phononic crystals", Journal of Applied Physics, 2009, pp. 053529-1 through 053529-5, vol. 106, American Institute of Physics.
Otsuka, P.H. et al., "Broadband evolution of phononic-crystal-waveguide eigenstates in real- and k-spaces", Scientific Reports, Nov. 27, 2013, pp. 1-5, www.nature.com.
Pennec, Y. et al., "Acoustic channel drop tunneling in a phononic crystal", Applied Physics Letters, Dec. 22, 2005, pp. 261912-1 through 261912-3, vol. 87, American Institute of Physics.
Sun, Jia-Hong et al., "Analyses of mode coupling in joined parallel phononic crystal waveguides", Physical Review B, May 24, 2005, pp. 174303-1 through 174303-8, vol. 71, The American Physical Society.
U.S. Appl. No. 16/258,439, filed Jan. 25, 2019, not yet published.

* cited by examiner $$-\varrho c_t^2 \nabla \times \nabla \times \mathbf{u} + \nabla\left[\nabla \cdot (\varrho c_l^2 \mathbf{u})\right] - (2\nabla \cdot \mathbf{u} + \mathbf{u} \cdot \nabla)\, \nabla(\varrho c_t^2) + \left[\nabla(\varrho c_t^2) \cdot \nabla\right] \mathbf{u} = \varrho\, \partial_t^2 \mathbf{u}.$$

*FIG. 1C*

PHONONIC CRYSTAL COUPLER

CROSS-REFERENCE TO RELATED APPLICATION(S)

The present application claims priority to and the benefit of U.S. Provisional Application No. 62/622,752, filed Jan. 26, 2018, entitled "PHONONIC CRYSTAL COUPLER", the entire content of which is incorporated herein by reference.

FIELD

One or more aspects of embodiments according to the present disclosure relate to acoustic signals, and more particularly to a coupler for guided acoustic waves.

BACKGROUND

Guided acoustic waves may be used in various applications, including filters and sensors. In such applications, it may be advantageous to couple waves from one acoustic waveguide to another. Although it may be possible to effect such coupling by converting acoustic waves into electrical or optical signals, using electrical or optical couplers to perform the coupling, and converting the signals back to acoustic waves, such approaches have various potential disadvantages, including the additional cost of transducers, and a degradation in performance that may result from noise produced by the transducers.

Thus, there is a need for an improved system for coupling acoustic energy between acoustic waveguides.

SUMMARY

According to some embodiments of the present invention, there is provided a phononic coupler, including: a sheet, including a plurality of standard reflectors, and a plurality of divergent reflectors defining, among the standard reflectors: a first waveguide, and a second waveguide, the phononic coupler having: a first port, at a first end of the phononic coupler, a second port, at the first end of the phononic coupler, and a third port, at a second end of the phononic coupler, the first waveguide having a first end at the first port, the second waveguide having: a first end at the second port, and a second end at the third port, the phononic coupler being configured to couple sound waves, at a frequency greater than 10 MHz and less than 100 GHz, received at the third port, to both the first port and the second port, at least 0.1% of the received sound wave power being coupled to the first port, and at least 0.1% of the received sound wave power being coupled to the second port.

In some embodiments: the sheet is composed of a material having a bulk propagation loss, for sound waves at a frequency greater than 10 MHz and less than 100 GHz, of less than 1 dB/micron, the sheet includes: a plurality of standard reflectors, each of the standard reflectors being associated with a respective grid point of a grid defined by a plurality of intersecting lines, each grid point being a respective intersection of two lines of the plurality of intersecting lines, the grid being locally periodic to within 5%, and having a local grid spacing, each of the standard reflectors having a center separated from the respective grid point of the standard reflector by at most 1% of the grid spacing, and a plurality of divergent reflectors, each associated with a respective grid point, the divergent reflectors defining a waveguide among the standard reflectors, each of the divergent reflectors being an absent reflector or a reflector that is smaller than one of the standard reflectors.

In some embodiments, within an interaction region of the phononic coupler: the grid spacing is constant to within 5%; and the second waveguide is: parallel, to within 10 degrees, to the first waveguide, and separated from the first waveguide by at most 10 times a maximum grid spacing in the interaction region.

In some embodiments, within the interaction region, the second waveguide is separated from the first waveguide by at most 5 times a maximum grid spacing in the interaction region.

In some embodiments, the interaction region has a length of at least 10 times the maximum grid spacing.

In some embodiments, the interaction region has a length of at least 30 times the maximum grid spacing.

In some embodiments, the interaction region has a length of at least 60 times the maximum grid spacing.

In some embodiments, the first waveguide has a curved portion outside of the interaction region, the waveguide having, at a first point within the curved portion, a centerline with a radius of curvature, at the first point along the waveguide, of less than 1,000 times a minimum separation between adjacent reflectors of the plurality of standard reflectors.

In some embodiments: the grid is defined by: a first plurality of parallel, straight lines, and a second plurality of parallel, straight lines, successive lines of the first plurality of parallel, straight lines are separated by the grid spacing at the first point, and successive lines of the second plurality of parallel, straight lines are separated by the grid spacing at the first point.

In some embodiments: each of the standard reflectors is a hole in the sheet having a radius differing from a standard hole radius by at most 5% each of the divergent reflectors is separated from the centerline of the waveguide by a transverse offset distance, each of the divergent reflectors is: a hole having a reduced radius smaller than the standard hole radius, the reduced radius differing by at most 5% from a radius determined by a waveguide profile radius function evaluated at the transverse offset distance, or an absence of a reflector.

In some embodiments, each of the divergent reflectors is: a hole, when the waveguide profile radius function evaluated at the transverse offset distance exceeds a threshold radius value, and an absence of a reflector otherwise.

In some embodiments, the waveguide profile radius function is a piecewise constant function.

In some embodiments, the waveguide profile radius function returns a first value when the transverse offset distance is less than a threshold offset distance, the threshold offset distance being less than the grid spacing at the first point.

In some embodiments, the waveguide profile radius function is a Lorentzian function.

In some embodiments, the waveguide profile radius function is function that is everywhere piecewise Lorentzian or piecewise constant.

In some embodiments, the phononic coupler further includes a fourth port, at the second end of the phononic coupler, the first waveguide having a second end at the fourth port.

In some embodiments, an acoustic output signal at the first port, in response to: a first acoustic input signal received at the third port and a second acoustic input signal received at the fourth port is a linear superposition of: an acoustic output signal that would be received at the first port if the first acoustic input signal were absent, and an acoustic output signal that would be received at the first port if the second acoustic input signal were absent.

In some embodiments, the phononic coupler has a coupling ratio of between 45% and 55%.

In some embodiments, the phononic coupler has a coupling ratio of between 70% and 90%.

In some embodiments, the phononic coupler has a coupling ratio of between 0.1% and 5%.

In some embodiments, the sound waves are waves of a kind selected from the group consisting of longitudinal waves, surface waves, Lamb waves, Love waves, Stoneley waves, Sezawa waves, and combinations thereof.

BRIEF DESCRIPTION OF THE DRAWINGS

These and other features and advantages of the present disclosure will be appreciated and understood with reference to the specification, claims, and appended drawings wherein:

FIG. 1C is a wave equation, according to an embodiment of the present disclosure;

DETAILED DESCRIPTION

The detailed description set forth below in connection with the appended drawings is intended as a description of exemplary embodiments of a phononic crystal coupler provided in accordance with the present disclosure and is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

Figure 1A:
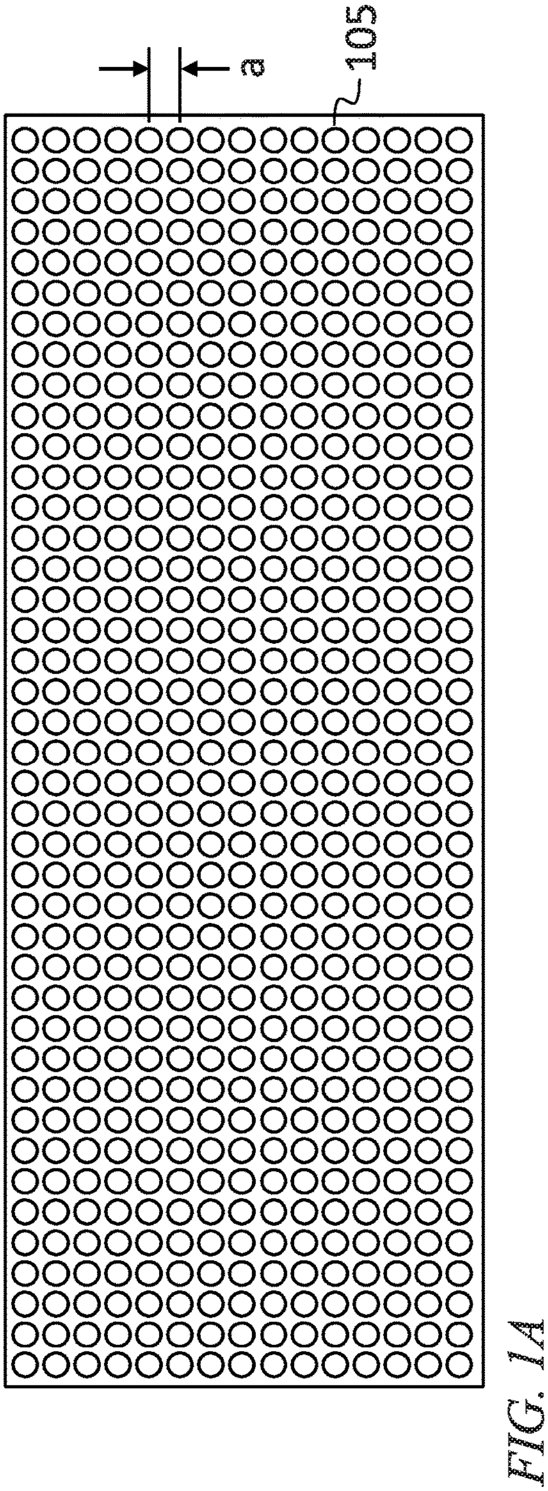
FIG. 1A is a top view of a phononic crystal, according to an embodiment of the present disclosure.

FIG. 1A shows a top view of a phononic crystal, in some embodiments. The phononic crystal may be a sheet of silicon carbide (SiC), silicon, diamond, aluminum nitride (AlN), glass, silicon nitride, quartz or the like (e.g., a sheet with a thickness between 10 nm and 100.000 microns, or between 100 nm and 10.000 microns, or having a thickness of 3.5 microns) with a plurality of holes 105 formed in it (e.g., by photolithographic etching) on a regular square grid as shown. The grid spacing (i.e., the "lattice constant", or the distance (labeled "a") between each hole and its nearest neighbors in the horizontal or vertical direction) may, for example, be about 9.45 microns, and the radius of each hole may be about 4.42 microns. In such an embodiment, the center frequency of the phononic crystal may be about 437 MHz. Each hole may act as a reflector, reflecting acoustic waves (e.g., sound waves at a frequency greater than 10 MHz and less than 100 GHz) travelling within the plane of the sheet. The sound waves may be longitudinal waves, surface waves (Rayleigh), Lamb waves, Love waves, Stoneley waves, Sezawa waves, or a combination of two or more of these kinds of waves. The phononic crystal may have the property that sound waves in a range of frequencies (e.g., between 430 MHz and 520 MHz) may not propagate horizontally within the sheet (i.e., in any direction parallel to the sheet); instead, any such sound waves incident on the sheet may be nearly entirely reflected (with the remaining acoustic power being absorbed, e.g., converted to heat energy through interactions with imperfections in the structure). This property may be referred to as “phononic band gap” as discussed in further detail below.

Figure 1B:
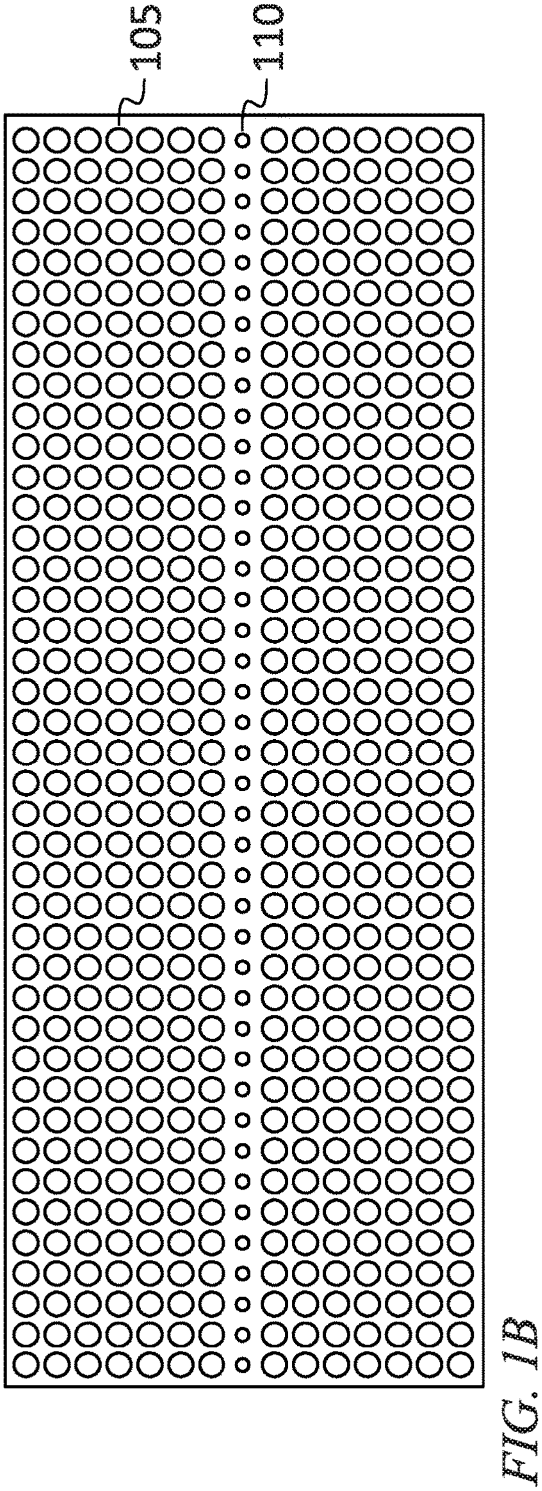
FIG. 1B is a top view of a phononic crystal waveguide, according to an embodiment of the present disclosure.

FIG. 1B shows a top view of a phononic crystal waveguide, in some embodiments. The structure of FIG. 1B differs from that of FIG. 1A in that in addition to a plurality of reflectors 105 like those of FIG. 1A (which may be referred to as “standard” reflectors), it includes a row of smaller reflectors 110 (which may be referred to as “divergent” reflectors). The standard reflectors 105 may all have substantially the same radius (e.g., each may have a radius differing from a standard hole radius by at most 5%). The effect of the presence of the divergent reflectors 110 may be to allow acoustic waves to propagate along the row of divergent reflectors 110, within the plane of the sheet. These acoustic waves may have a transverse mode shape that is largely confined to a narrow region including the divergent reflectors 110, and that has only evanescent tails extending into the regions on either side of the row of divergent reflectors 110. As such, the divergent reflectors 110 may define a waveguide among the standard reflectors 105. The waveguide may be a single-mode waveguide, i.e., it may allow only one transverse mode to propagate. In some embodiments, the reflectors are not round holes but are instead other features that locally affect the propagation of acoustic waves so that a fraction of the acoustic energy in such a wave is reflected. Such features may be holes that are not round (e.g., crosses, snowflakes, double holes, etc.) or local changes in the thickness of the sheet, or local changes in the composition of the sheet, for example. The “size” of such a reflector may be defined to be the diameter of a cylindrical hole with the same scattering cross section for acoustic waves. In other analogous embodiments, the grid may be a triangular grid, a hexagonal grid, or a rectangular grid, instead of being a square grid.

Figure 1D:
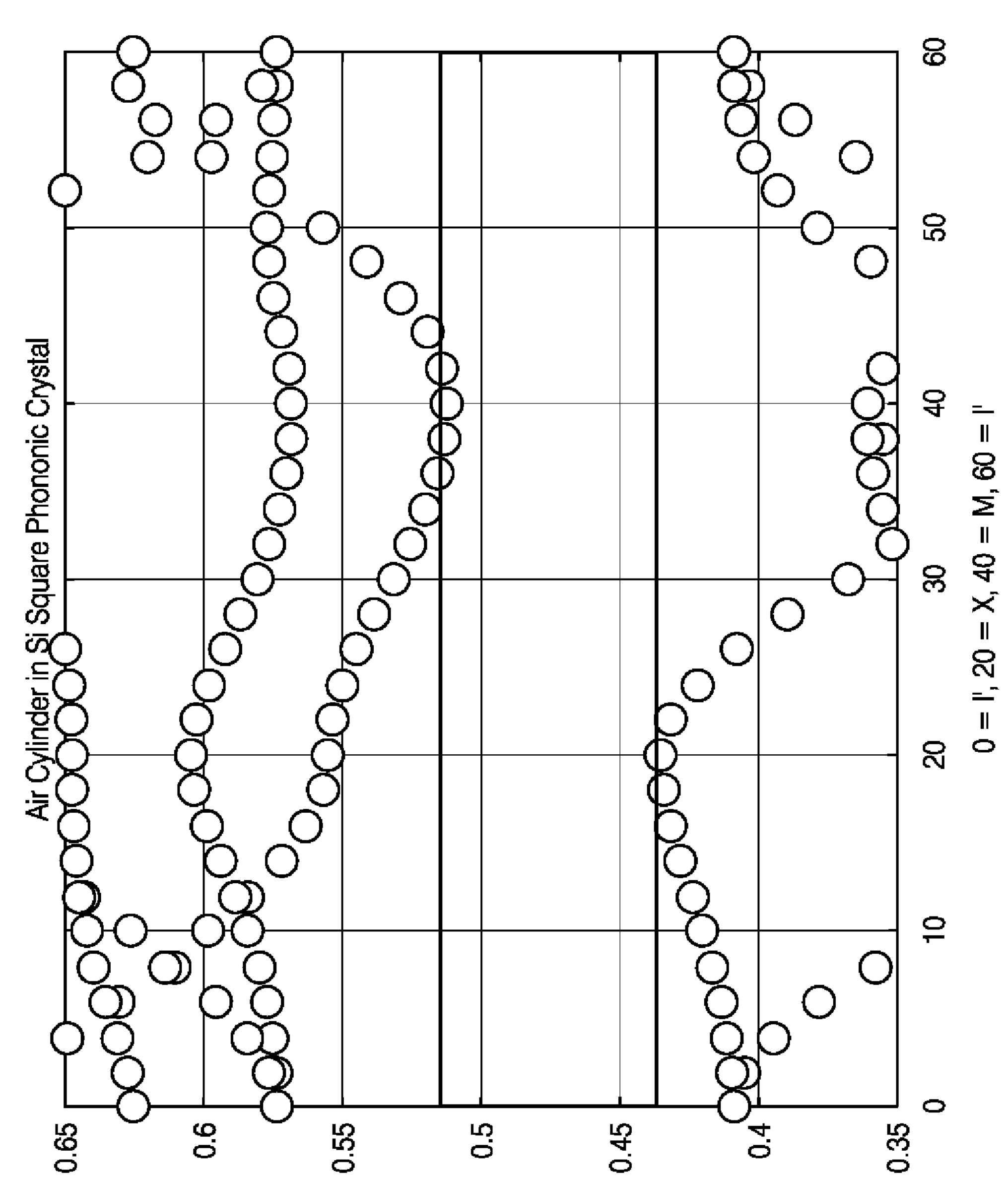
FIG. 1D is a dispersion diagram, according to an embodiment of the present disclosure.
Figure 1E:
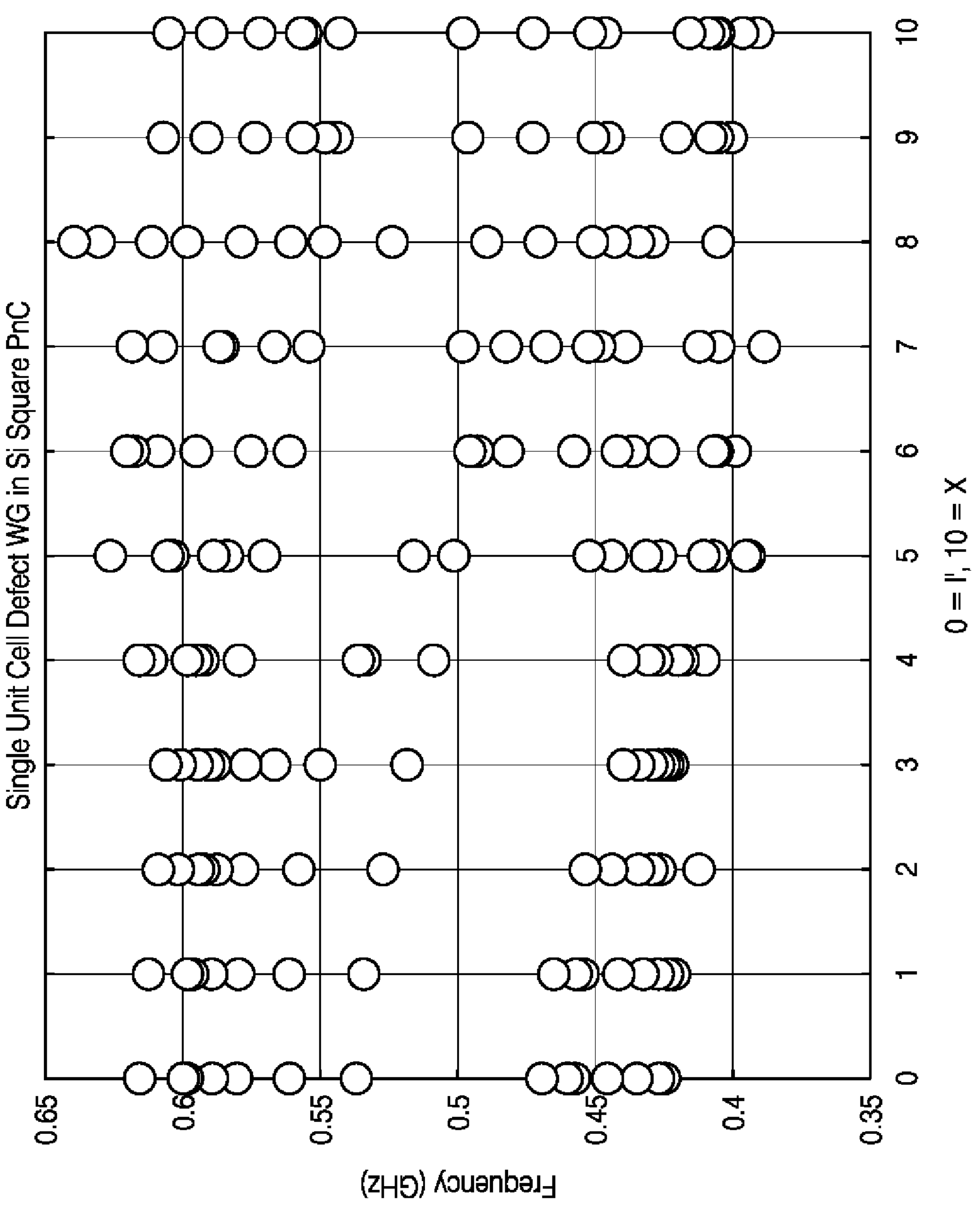
FIG. 1E is a dispersion diagram, according to an embodiment of the present disclosure.

FIG. 1C shows the wave equation for propagation of acoustic waves in an elastic material, with rho being the density of the material, $c_t$ and $c_l$ being the speed of sound for transverse and longitudinal waves respectively, and u being the local instantaneous displacement of the material. FIG. 1D shows the dispersion relation for a phononic crystal such as that of FIG. 1A. The above-mentioned bandgap is evident as a region (corresponding to a frequency range from about 430 MHz to about 520 MHz) from which solutions of the wave equation for traveling waves are absent. FIG. 1E shows the dispersion relation for a phononic crystal with a waveguide, such as that of FIG. 1B; the absence of a bandgap corresponds to the ability of acoustic waves to propagate as guided, confined modes, over a range of frequencies, along the waveguide. In other embodiments, greater confinement of the acoustic mode to the waveguide region may be achieved by either perturbing the lattice spacing or the hole size—leading to a change in the local r/a ratio, where r is radius and a is lattice constant.

Figure 1F:
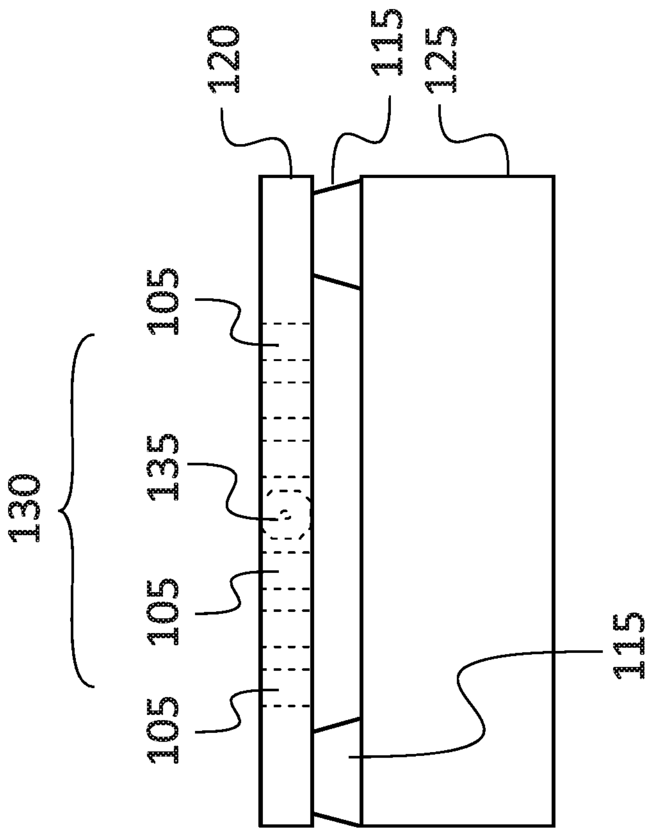
FIG. 1F is a cross-sectional view of a suspended membrane phononic crystal architecture, according to an embodiment of the present disclosure.

FIG. 1F shows a side cross sectional view of a waveguide structure similar to that of FIG. 1B, as well as a set of anchors 115 that may be used to secure a sheet 120 to a support structure, e.g., a substrate 125. In such an embodiment, the phononic crystal waveguide 130 is formed by etching a periodic pattern of standard reflectors 105 (e.g., holes) in the sheet 120. The periodic structure forms a phononic bandgap and excludes phonon propagation over a range of frequencies in some areas, thus forming a phononic crystal waveguide 130 that supports a phononic mode 135. In a suspended membrane phononic crystal architecture, such as that shown in FIG. 1F, the air above and below the sheet 120 confines phonons in the vertical dimension. Such a structure may be inherently robust (e.g., able to withstand significant shock and vibration).

Figure 1G:
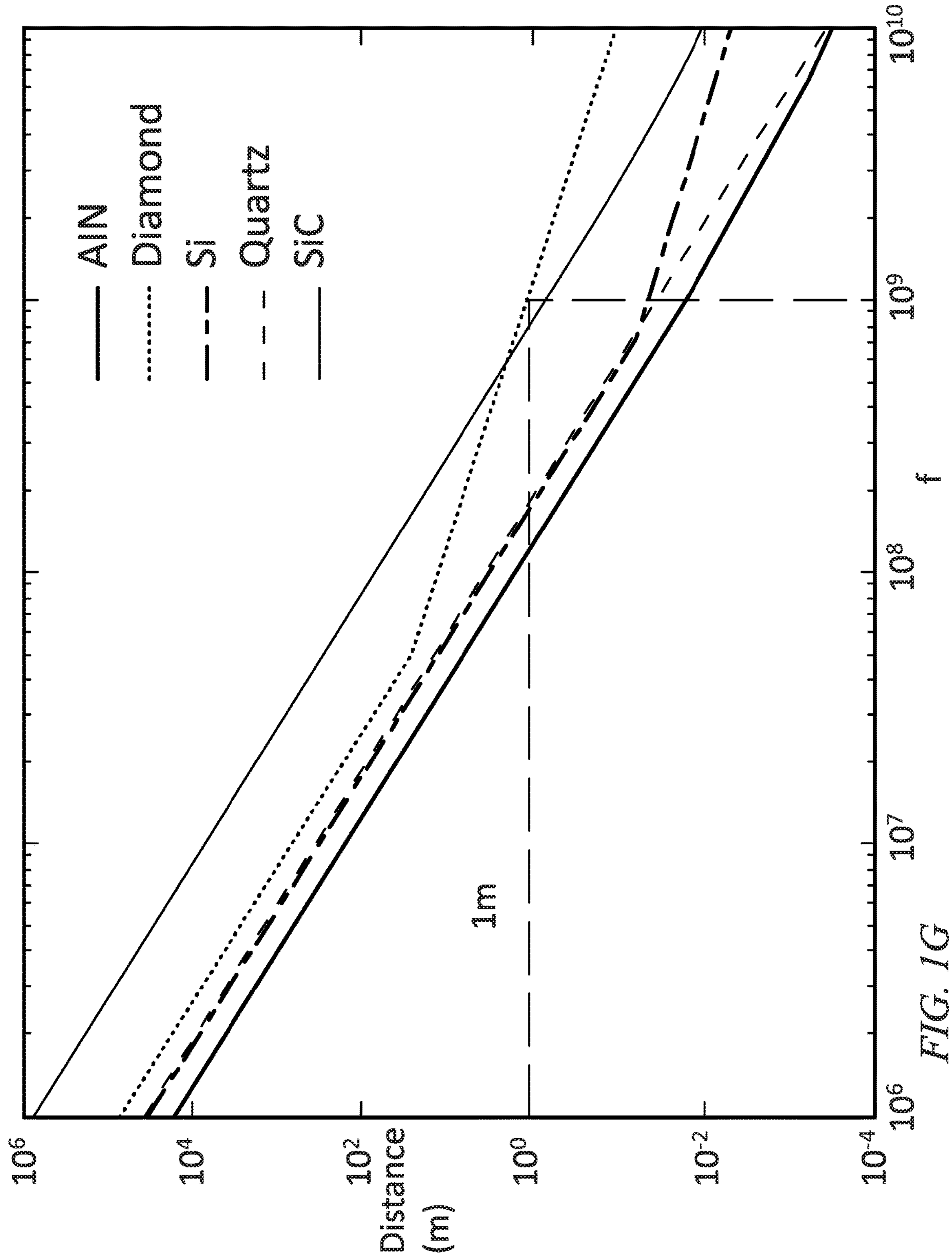
FIG. 1G is a graph of (1/e) propagation lengths as a function of frequency, according to an embodiment of the present invention.

FIG. 1G shows the propagation constants of phononic crystal waveguides in several acoustic materials that may be used to fabricate phononic crystal waveguides. A meter of propagation may be achievable in both diamond and SiC phononic waveguides. The ability of waveguide modes to propagate long distances relative to the wavelength of the propagating waves may make possible the construction of various useful structures, such as resonators (discussed in further detail below). Propagation loss of less than 1 dB/micron (μm) may be sufficiently low for fabricating useful structures, in some applications.

Figure 1H:
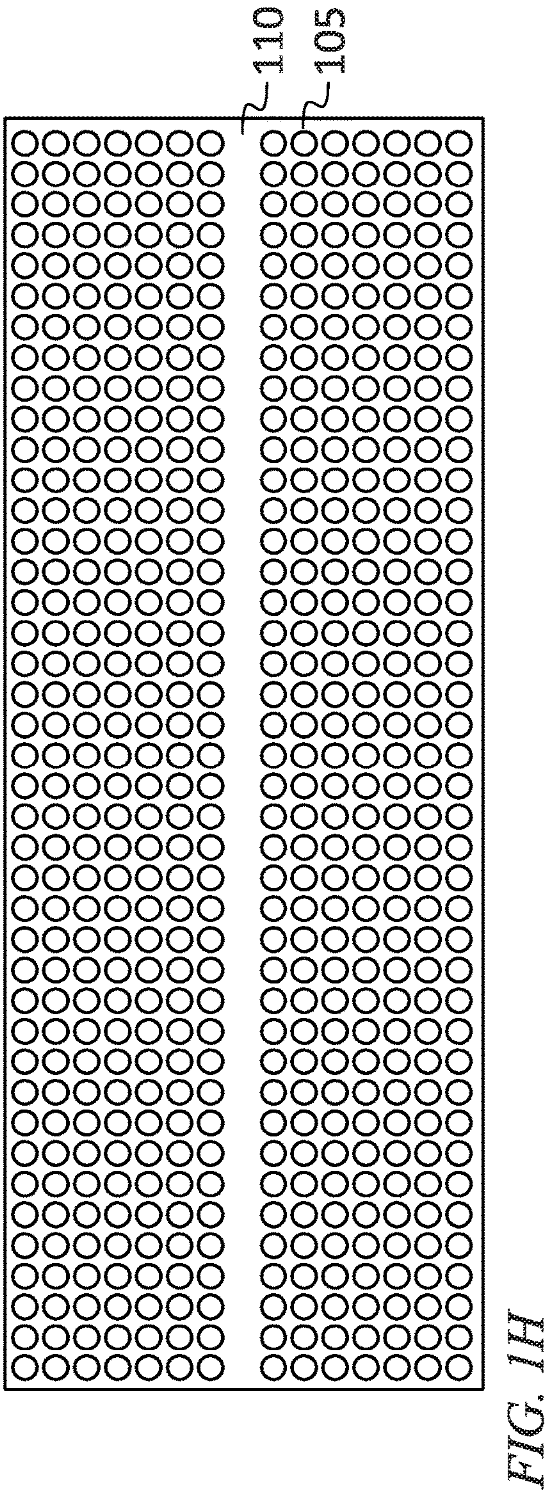
FIG. 1H is a top view of a phononic crystal waveguide, according to an embodiment of the present disclosure.
Figure 1I:
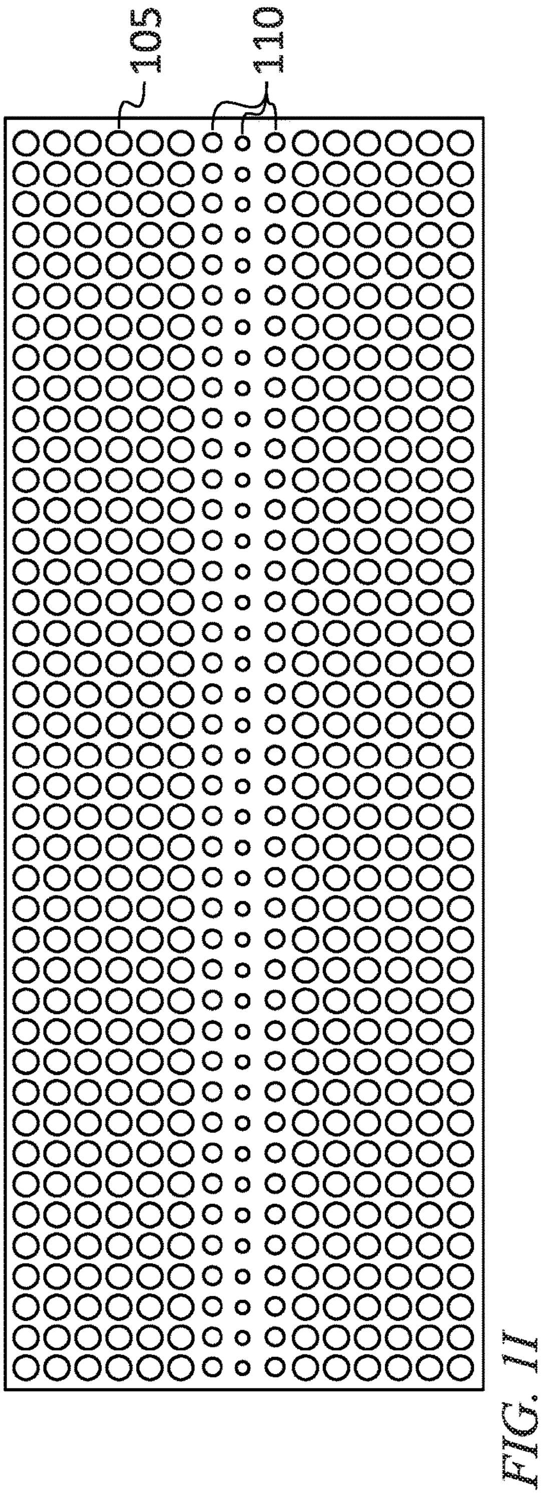
FIG. 1I is a top view of a phononic crystal waveguide, according to an embodiment of the present disclosure.

In some embodiments, the divergent reflectors 110 may be grid points at which the reflectors, instead of being smaller than the standard reflectors 105 (as in FIG. 1B) are entirely absent, as shown in FIG. 1H. Accordingly, as used herein, the term “divergent reflector” encompasses any absent reflectors, at positions at which the phononic crystal, were it uniform, would include a standard reflector 105. In other embodiments, the waveguide may include more than one row of divergent reflectors 110, e.g., it may include two rows of divergent reflectors 110, or three rows of divergent reflectors 110 as shown in FIG. 1I, or more than three rows of divergent reflectors 110.

Figure 2A:
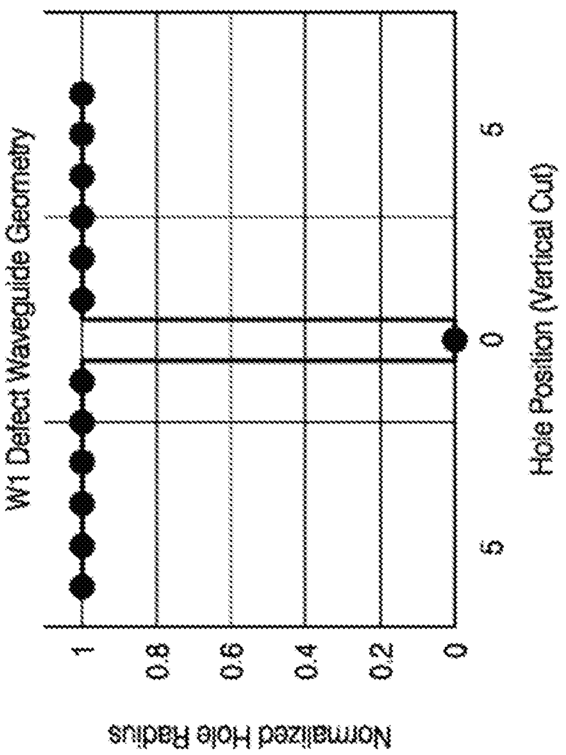
FIG. 2A is a graph of a waveguide profile radius function, according to an embodiment of the present disclosure.
Figure 2B:
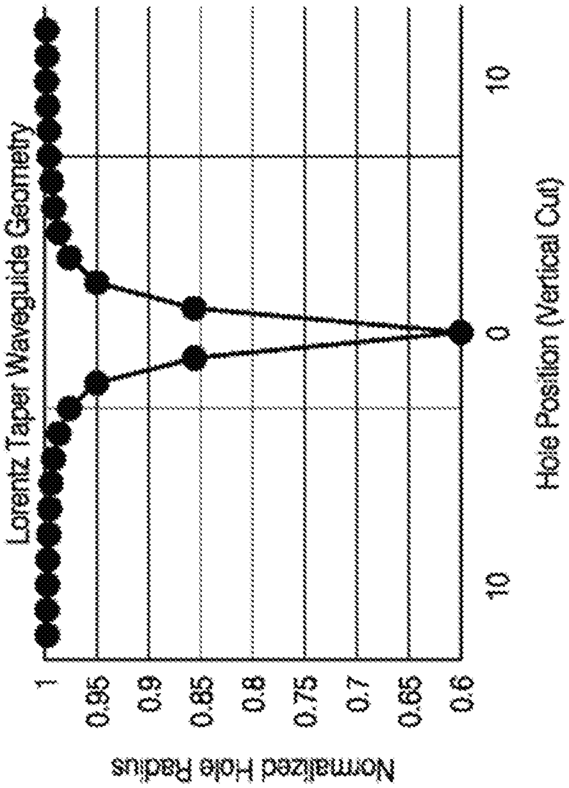
FIG. 2B is a graph of a waveguide profile radius function, according to an embodiment of the present disclosure.
Figure 2C:
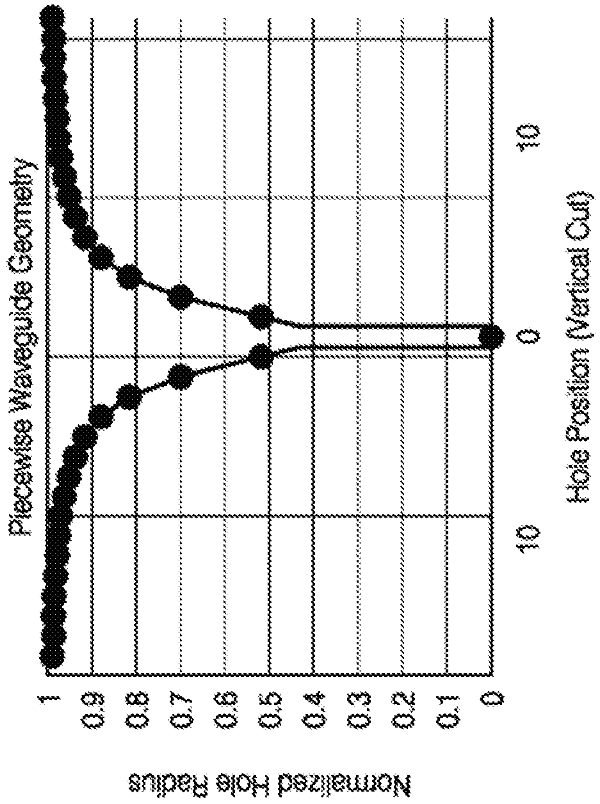
FIG. 2C is a graph of a waveguide profile radius function, according to an embodiment of the present disclosure.

In some embodiments in which the reflectors are cylindrical holes in the sheet, the radius of each of the divergent reflectors 110 is determined by a function referred to as a waveguide profile radius function, which takes, as an argument, the distance (or “transverse offset distance”) of the divergent reflector 110 from the centerline of the waveguide and returns the radius of the divergent reflector 110. FIGS. 2A-2C show three examples of normalized waveguide profile radius function, each of which is a waveguide profile radius function normalized to the radius of a standard reflector. In some embodiments, the waveguide profile radius function is a piecewise constant function, e.g., having a constant value of zero over a range of values that includes the centerline of the waveguide, as shown in FIG. 2A; such a waveguide profile radius function may correspond to the embodiment of FIG. 1H, in which the divergent reflectors 110 along the centerline of the waveguide are entirely absent. In other embodiments, the constant value is greater than zero but less than 1; such a waveguide profile radius function may correspond to the embodiment of FIG. 1B, in which the divergent reflectors 110 along the centerline of the waveguide are present but smaller than the standard reflectors 105.

Referring to FIG. 2B, in some embodiments the waveguide profile radius function may be a Lorentzian function, with the functional form $$r = r_{std}\left[1 - \frac{(1 - \text{mincenter})}{\left[1 + \left(\frac{D_{transverse\ offset}}{\text{gamma}}\right)^2\right]}\right]$$

where mincenter is the value of the waveguide profile radius function (relative to the radius of the standard reflectors 105) at the centerline of the waveguide, $D_{transverse\ offset}$ is the distance of the divergent reflectors 110 from the centerline (i.e., the transverse offset distance), and gamma is a width parameter, which for FIG. 2B is equal to 0.75. In some embodiments the normalized waveguide profile radius function is piecewise Lorentzian and piecewise constant, as shown for example in FIG. 2C.

In some embodiments, the use of a waveguide profile radius function to determine the radius of each of the divergent reflectors 110 in a design may result in a divergent reflector 110 being assigned a radius, by the waveguide profile radius function, that is smaller than a threshold radius value and too small to be reliably fabricated. In such a case, a divergent reflector 110 with zero radius (i.e., no hole) may be fabricated at the location at which the small divergent reflector would otherwise have been formed.

Figure 3A:
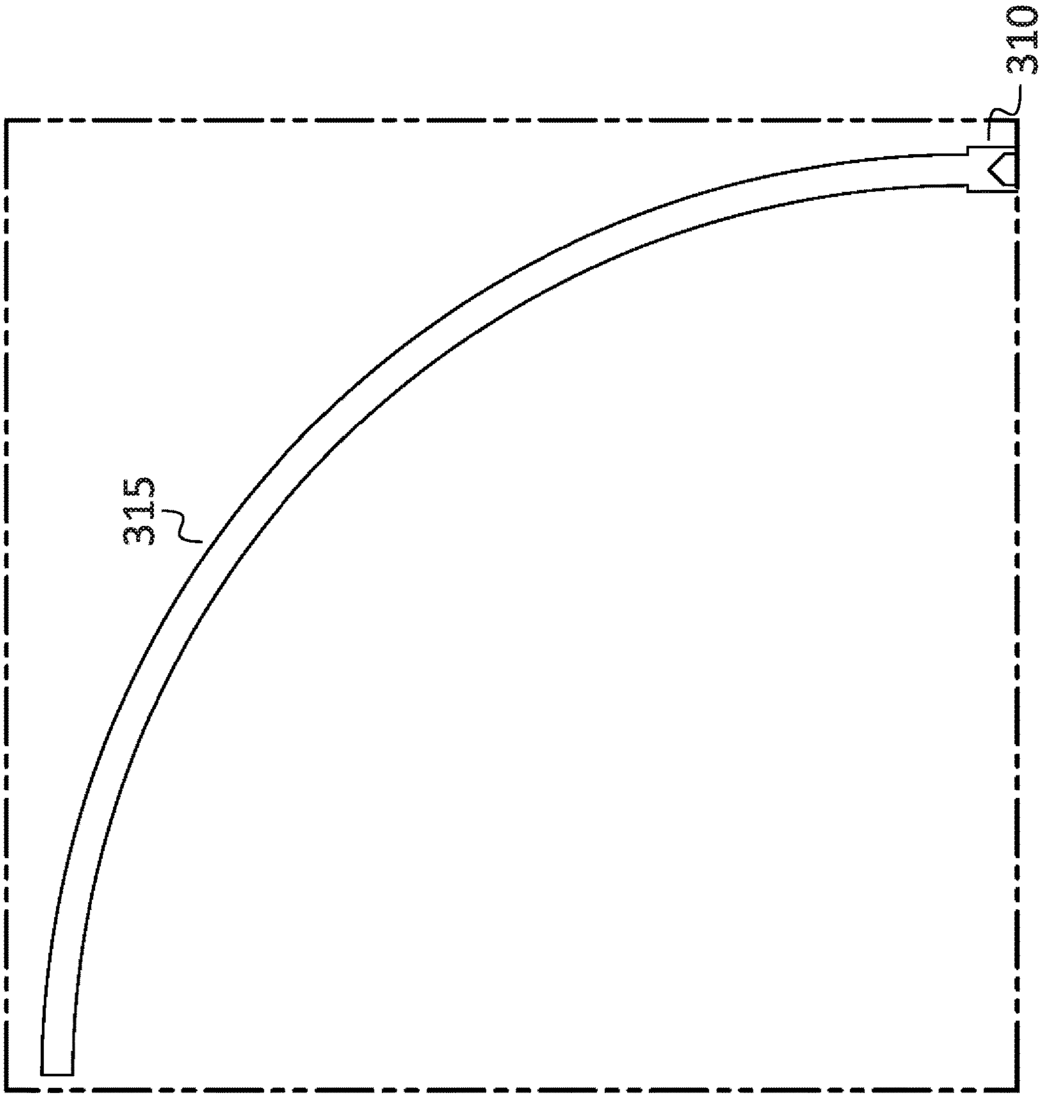
FIG. 3A is a top view of a curved phononic crystal waveguide and launch region, according to an embodiment of the present invention.
Figure 3B:
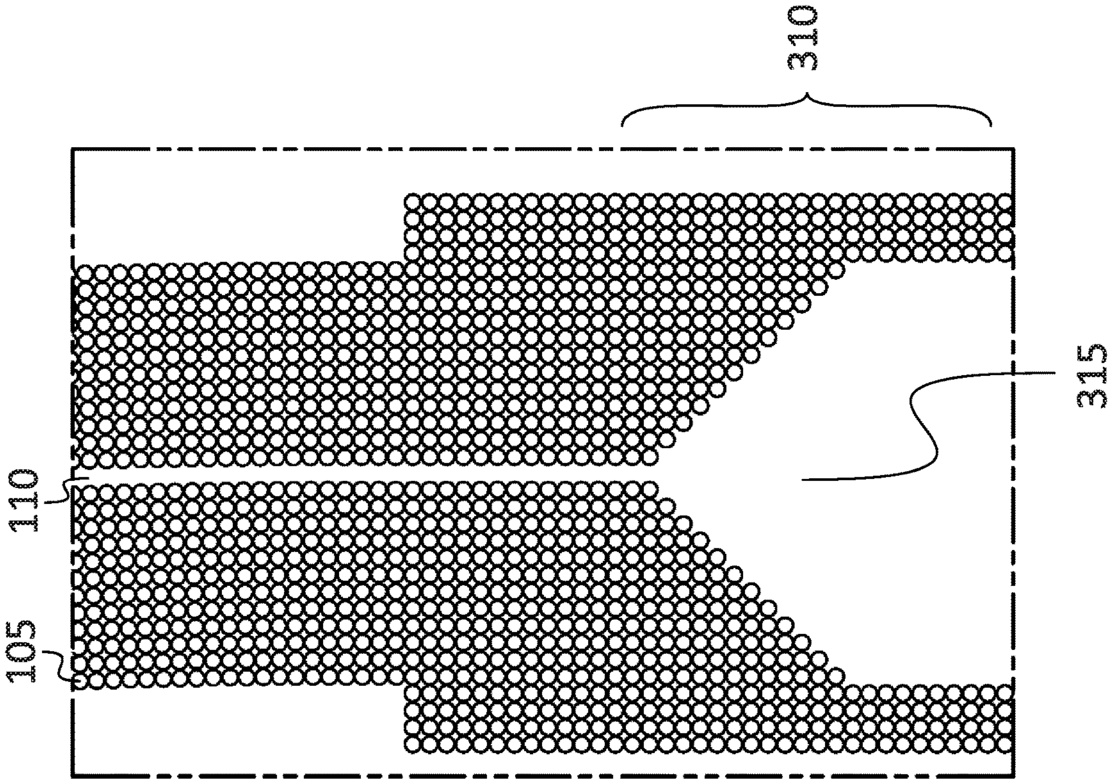
FIG. 3B is an enlarged top view of the launch region of FIG. 3A, according to an embodiment of the present invention.
Figure 3C:
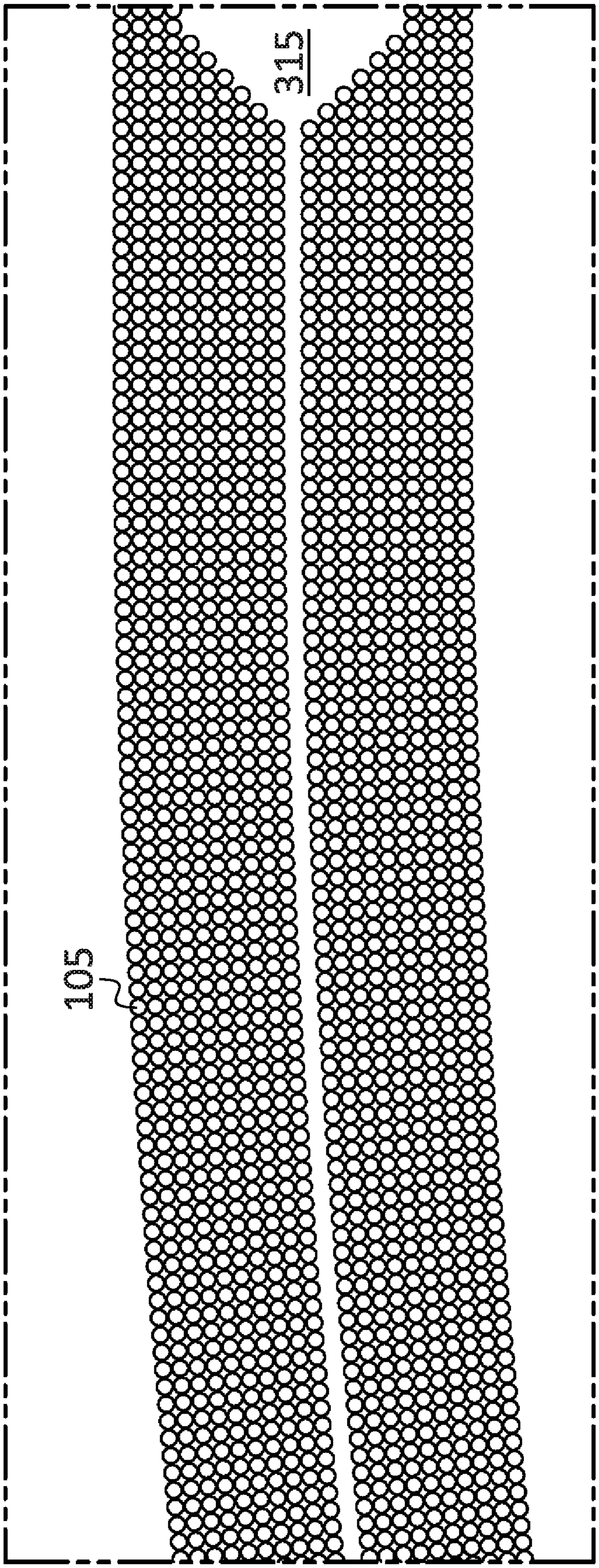
FIG. 3C is an enlarged top view of the beginning region of the curved phononic crystal waveguide of FIG. 3A, according to an embodiment of the present invention.
Figure 3D:
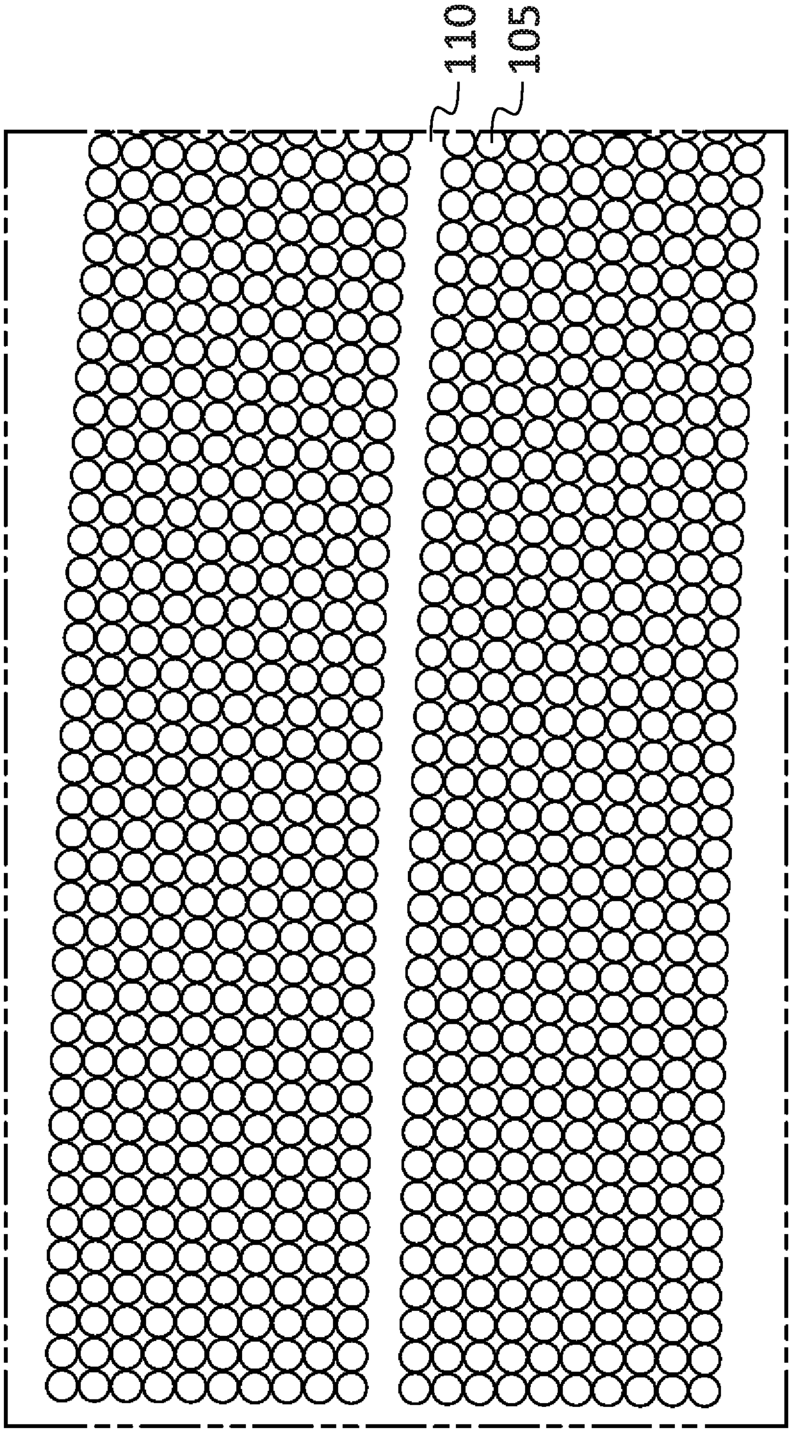
FIG. 3D is an enlarged top view of the end region of the curved phononic crystal waveguide of FIG. 3A, according to an embodiment of the present invention.

The principles described above for the design and fabrication of a straight phononic crystal waveguide may be extended, in some embodiments, to the design and fabrication of curved phononic crystal waveguides (e.g., a phononic crystal waveguide with a radius of curvature less than 1,000 times the grid spacing). FIG. 3A shows an example of such a curved waveguide, having a launch region 310 and a curved portion in the shape of a quarter-circle. Guided acoustic waves launched in the launch region 310 may change their direction of propagation by about 90 degrees by propagating along the curved portion. The launch region 310, shown in FIG. 3B, may include a tapered portion within which substantially unguided waves are coupled to the single guided mode capable of propagating within the phononic crystal waveguide. FIG. 3C (the view of which is rotated 90 degrees with respect to FIGS. 3A and 3B) shows an initial portion of the curved phononic crystal waveguide of FIG. 3A, and FIG. 3D shows the end portion. As mentioned above, when the waves launched in the launch region 310 reach the end portion shown in FIG. 3D, the direction of propagation is perpendicular, or nearly perpendicular, to that in the beginning portion of the curved phononic crystal waveguide.

The curved phononic crystal waveguide of FIGS. 3A-3D is fabricated using a curved grid. The grid is defined by intersections between of gridlines a first plurality of gridlines, and gridlines of a second plurality of gridlines, the first plurality of gridlines being concentric arcs, and the second plurality of gridlines being radial lines. Each of the standard reflectors 105 is on a grid point defined by the intersection of (i) a gridline of the first plurality of gridlines and (ii) a gridline of the second plurality of gridlines. The example of FIGS. 3A-3D involves a grid that is not perfectly periodic, but it is locally periodic (e.g., locally periodic to 5% or better) in the sense that in any small neighborhood (e.g., a 3×3 neighborhood of grid points) the grid spacing is constant to 5% or better. Further, in this embodiment (and in the other embodiments described herein), limitations in the fabrication process may result in some of the standard reflectors 105 or some of the divergent reflectors 110 being at locations that are offset (e.g., offset by up to 1% of the grid spacing) from their respective grid points.

FIGS. 4A-4D show a phononic crystal waveguide having the shape of a Lissajous curve. The two end portions (shown in FIGS. 4B and 4C) each have a direction of propagation that is substantially parallel to the grid (a horizontal direction of propagation, in the views of FIGS. 4A-4C), and the central portion shown in FIG. 4D has a direction of propagation that is oblique to the grid.

The curved phononic crystal waveguide of FIGS. 4A-4D is fabricated using a square grid. As used herein, a "square grid" is a grid defined by intersections between gridlines of a first plurality of gridlines, and gridlines of a second plurality of gridlines, the first plurality of gridlines being parallel, uniformly spaced, straight lines, with the spacing between adjacent lines being the grid spacing (i.e., the lattice constant "a") and the second plurality of gridlines being parallel, uniformly spaced, straight lines, with the spacing between adjacent lines also being the grid spacing, each of the second plurality of gridlines being perpendicular to the gridlines of the first plurality of gridlines. The waveguide centerline, as mentioned above, is a Lissajous curve. In the embodiment of FIGS. 4A-4D the waveguide profile radius function is a piecewise constant function. As a result, each of the divergent reflectors 110 has a smaller radius than the standard reflectors 105, the radii of all of the divergent reflectors 110 are the same, and the divergent reflectors are on grid points that are separated from the centerline of the phononic crystal waveguide by a distance (referred to as the transverse offset distance) that is less than a threshold offset distance (which, in embodiment of FIGS. 4A-4D, is one-half the grid spacing).

Figure 4A:
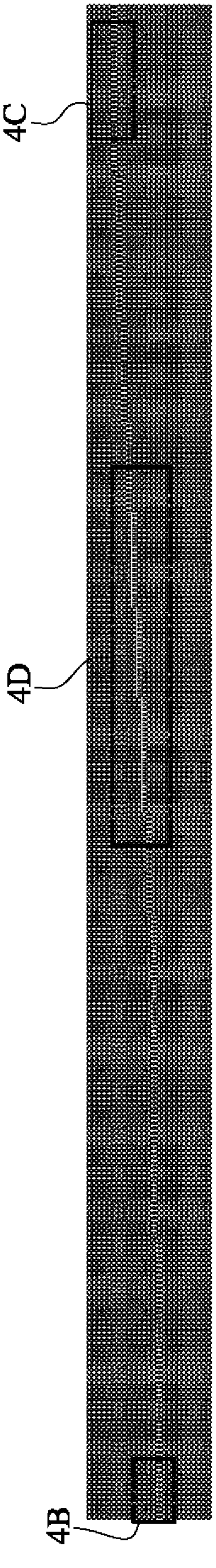
FIG. 4A is a top view of a curved phononic crystal waveguide, according to an embodiment of the present invention.
Figure 4B:
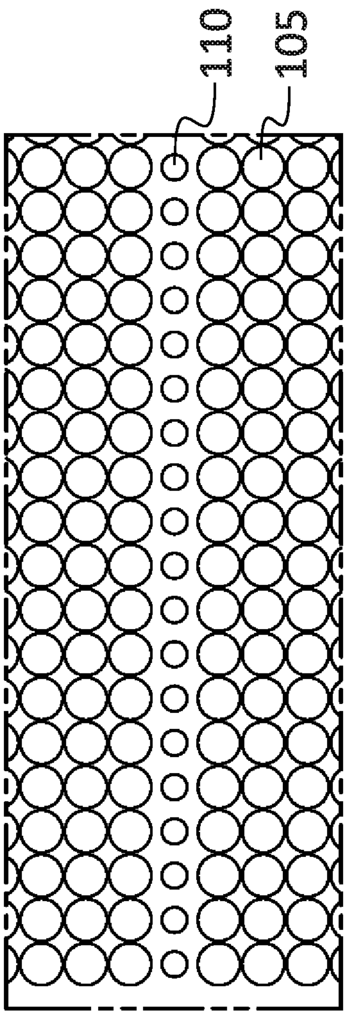
FIG. 4B is an enlarged top view of a portion of the curved phononic crystal waveguide of FIG. 4A, according to an embodiment of the present invention.
Figure 4C:
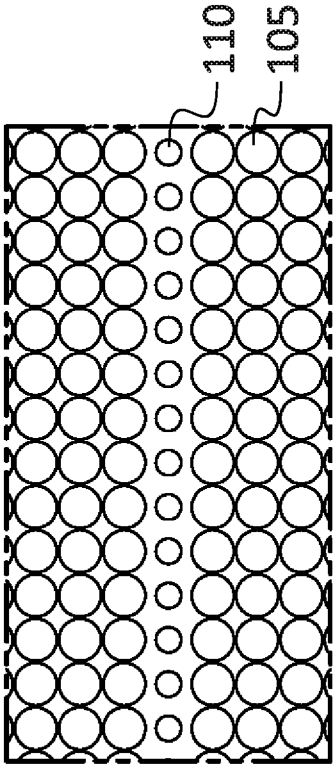
FIG. 4C is an enlarged top view of a portion of the curved phononic crystal waveguide of FIG. 4A, according to an embodiment of the present invention.
Figure 4D:
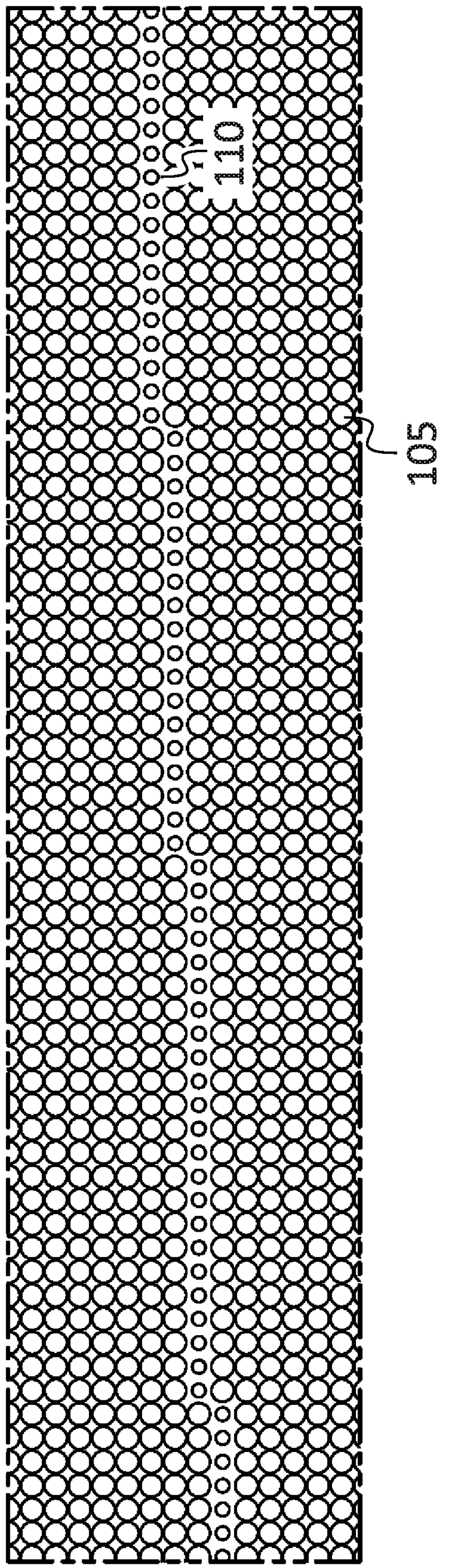
FIG. 4D is an enlarged top view of a portion of the curved phononic crystal waveguide of FIG. 4A, according to an embodiment of the present invention.

As may be seen from FIG. 4D, the use of a piecewise constant waveguide profile radius function when the grid is a square grid may result in discontinuities in the set of divergent reflectors 110, especially when, as in FIG. 4D, the phononic crystal waveguide is nearly parallel to the first or second plurality of gridlines. In such a case, a portion of the phononic crystal waveguide has a large number (e.g. more than 10) divergent reflectors 110 on a first gridline, and an adjacent portion of the phononic crystal waveguide has a similarly large number on a second gridline that is offset by one from the first gridline. The presence of such discontinuities may result in reflections or loss in the waveguide, or both. The effects of such discontinuities may be mitigated by using a smoother waveguide profile radius function, such as a Lorentzian waveguide profile radius function.

Figure 5A:
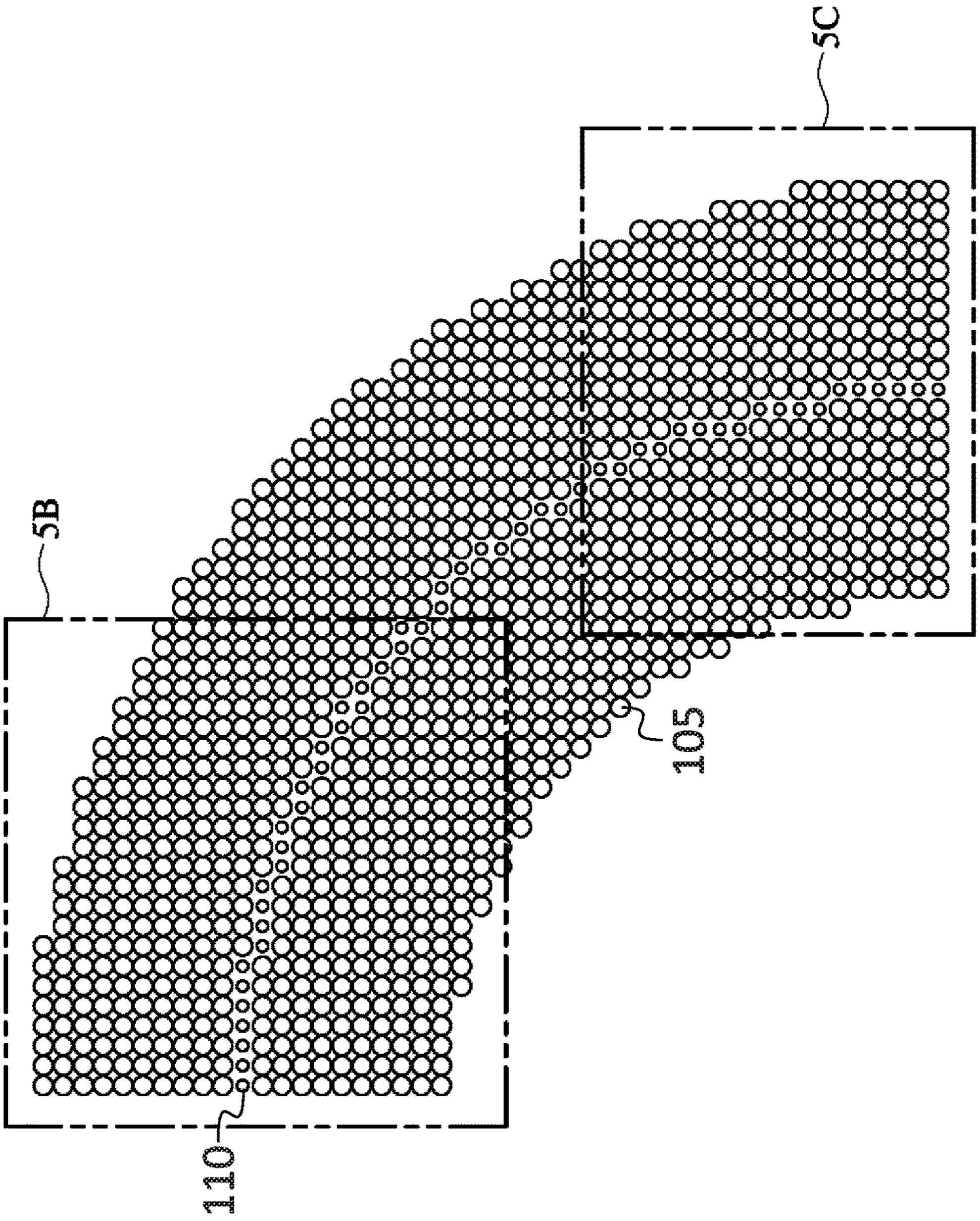
FIG. 5A is a top view of a curved phononic crystal waveguide, according to an embodiment of the present invention.
Figure 5B:
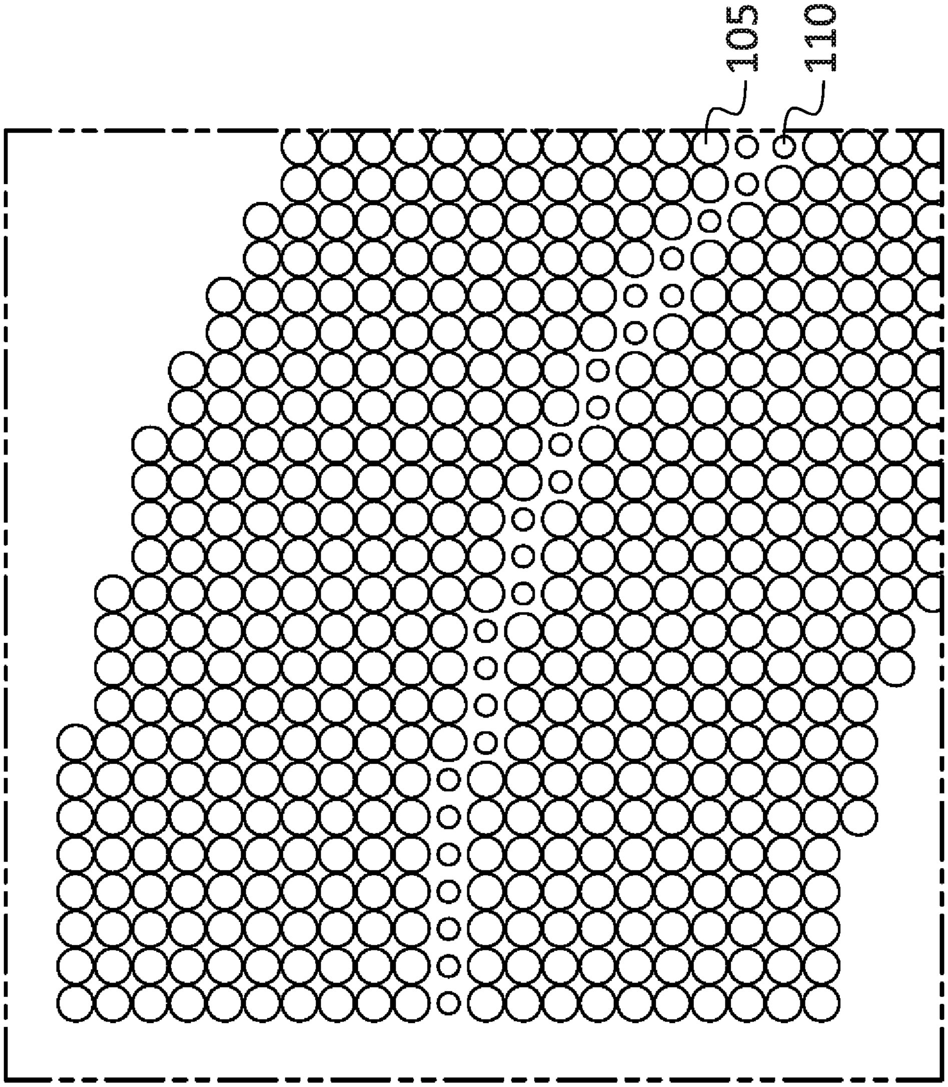
FIG. 5B is an enlarged top view of a portion of the curved phononic crystal waveguide of FIG. 5A, according to an embodiment of the present invention.
Figure 5C:
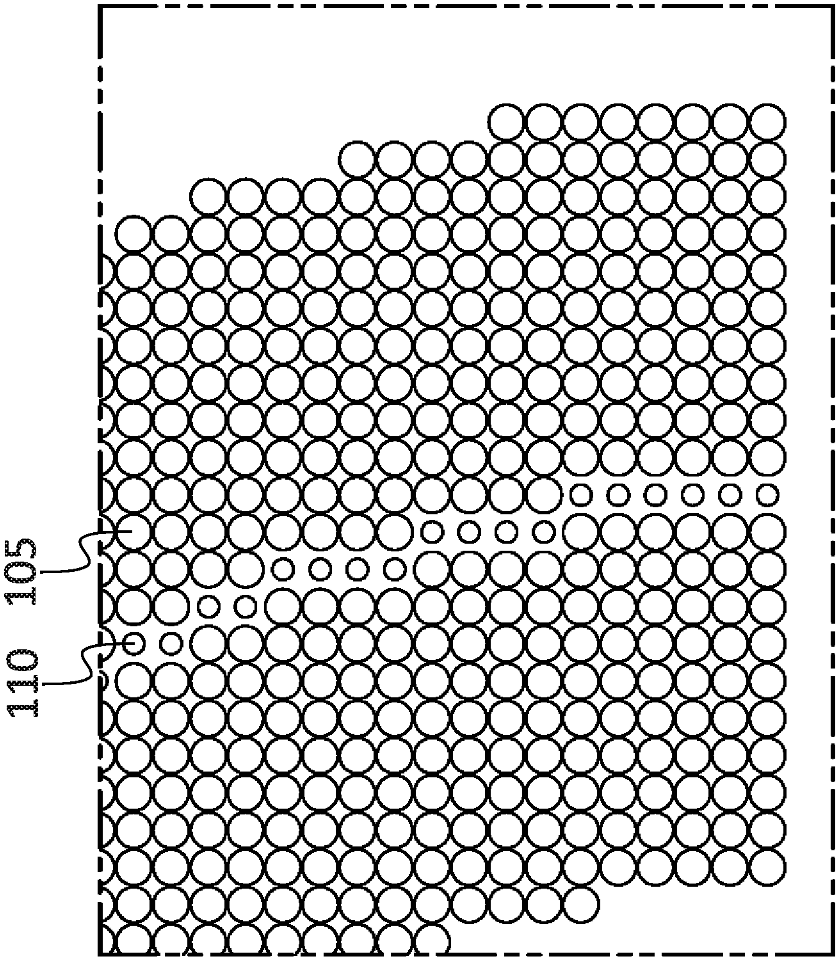
FIG. 5C is an enlarged top view of a portion of the curved phononic crystal waveguide of FIG. 5A, according to an embodiment of the present invention.

FIG. 5A shows a curved phononic crystal waveguide that, like the waveguide of FIG. 3A, has the shape of a quarter-circle. The phononic crystal waveguide of FIG. 5A has a square grid, however, unlike the phononic crystal waveguide of FIG. 3A, which has a curved grid. FIGS. 5B and 5C are enlarged views of portions of a first end and a second end of the curved phononic crystal waveguide of FIG. 5A. The use of a square grid may make possible the fabrication of a waveguide with a significantly smaller radius of curvature than may be readily possible with a curved phononic crystal waveguide fabricated with a curved grid. Like the curved phononic crystal waveguide of FIGS. 4A-4D, the curved phononic crystal waveguide of FIGS. 5A-5C exhibits discontinuities in the divergent reflectors 110, and, as in the case of the waveguide of FIGS. 4A-4D, the effects of such discontinuities may be mitigated by using a smoother waveguide profile radius function, such as a Lorentzian waveguide profile radius function.

Figure 6A:
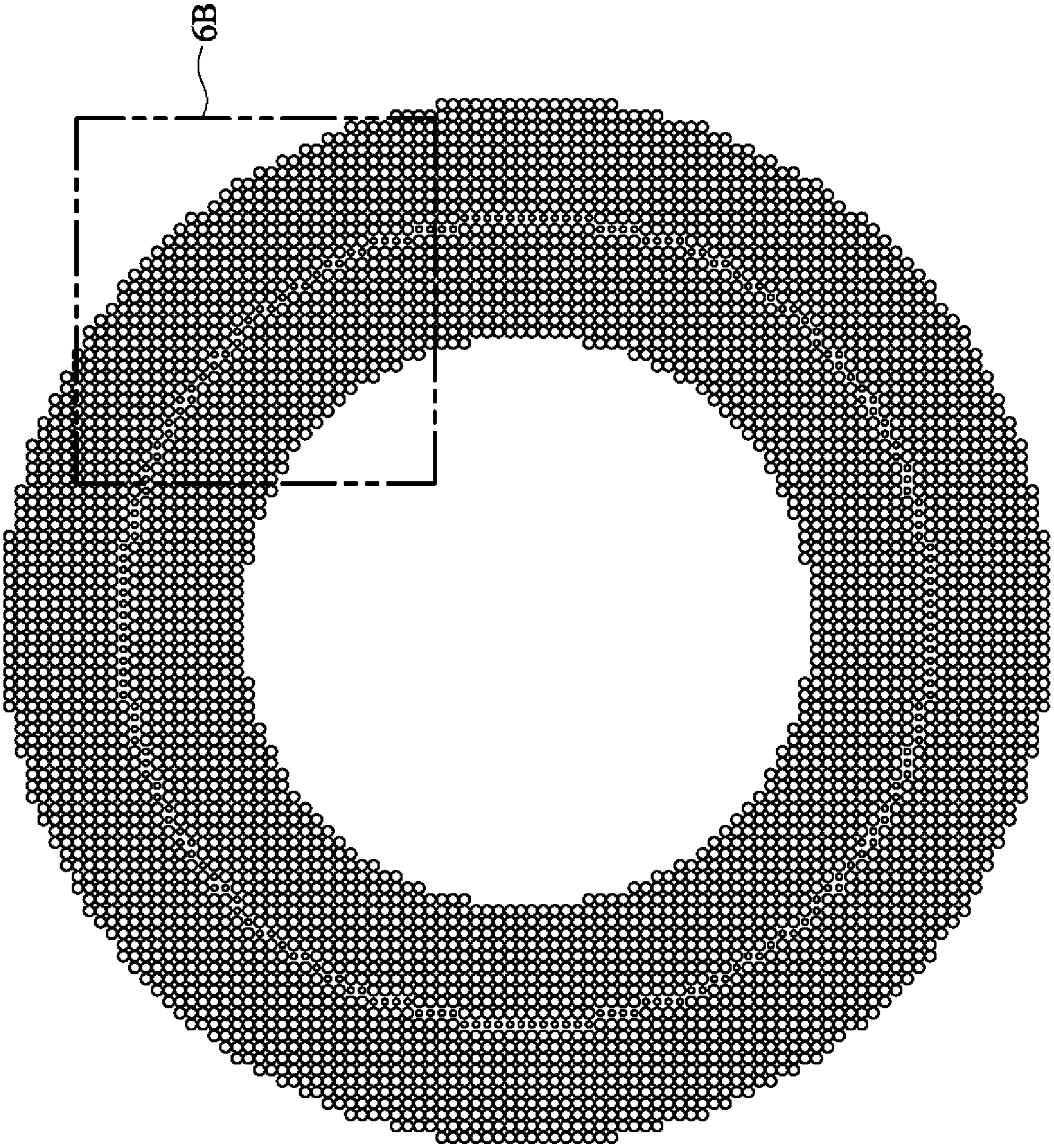
FIG. 6A is a top view of a phononic resonator, according to an embodiment of the present invention.
Figure 6B:
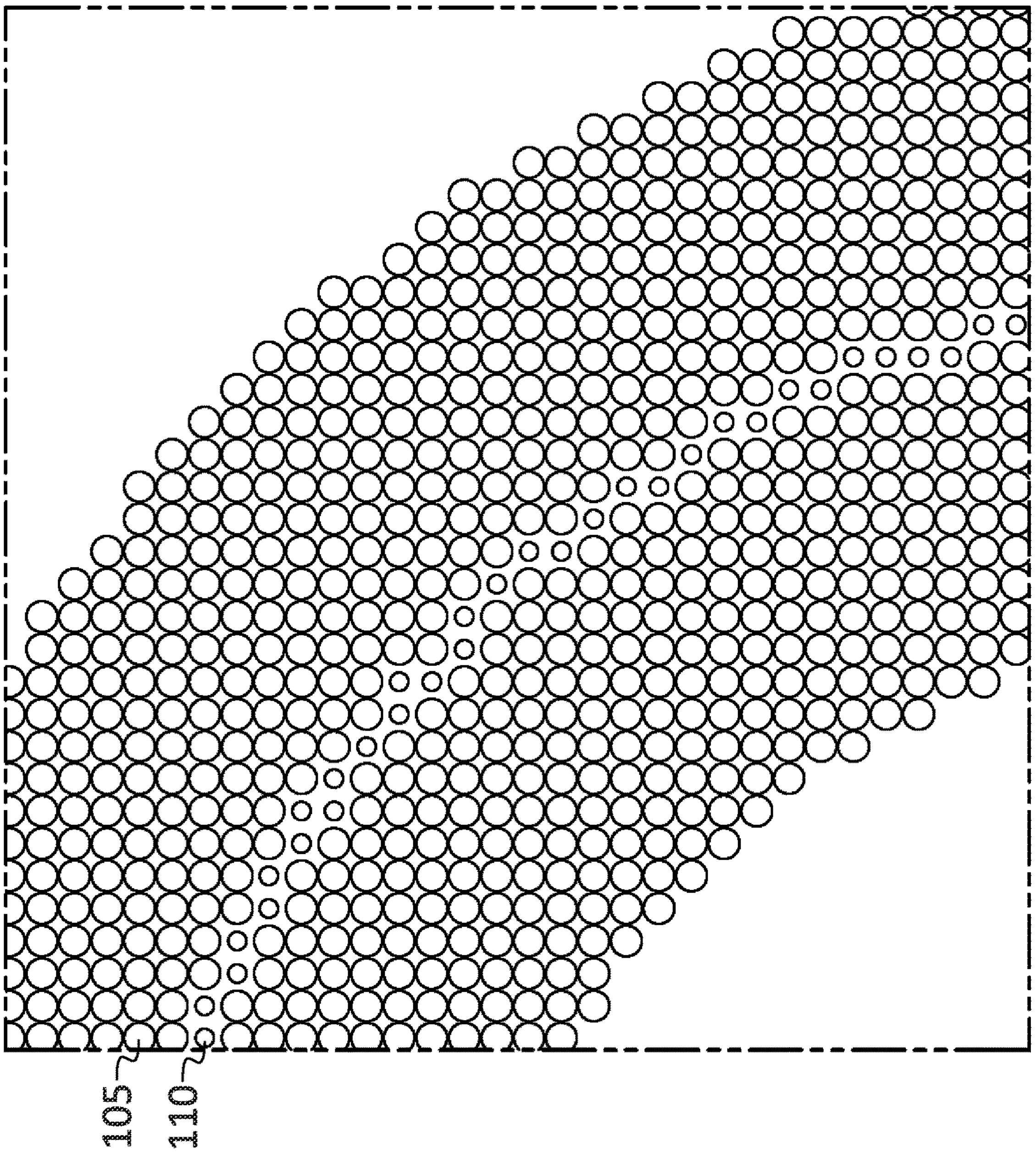
FIG. 6B is an enlarged top view of a portion of the phononic resonator of FIG. 6A, according to an embodiment of the present invention.

Curved phononic crystal waveguides may be used to fabricate various useful structures. Referring to FIG. 6A, for example, a curved phononic crystal waveguide may form a circular phononic resonator as shown. FIG. 6B shows an enlarged view of a portion of the circular phononic resonator of FIG. 6A.

Figure 7:
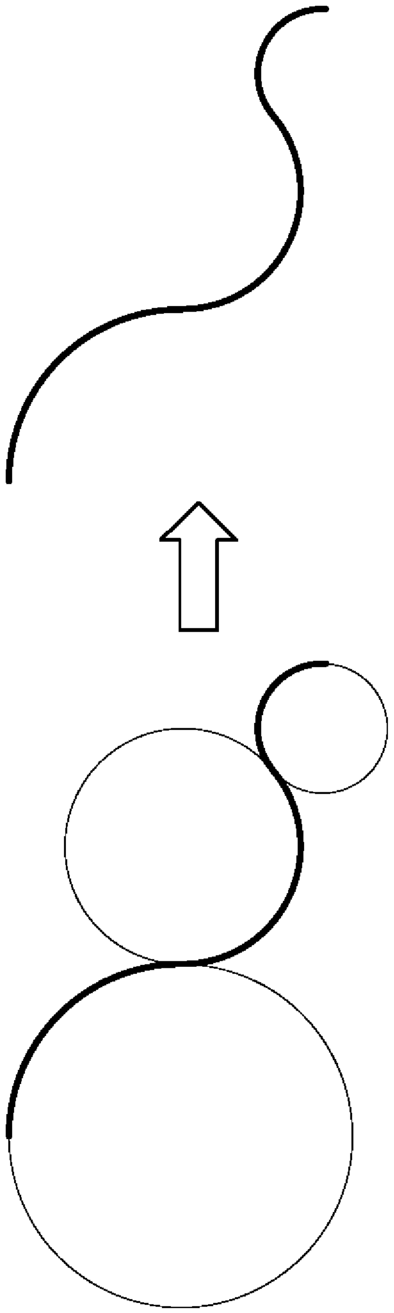
FIG. 7 shows two top views of a curved phononic crystal waveguide, according to an embodiment of the present invention.

Various other waveguide shapes may be formed by cascading a plurality of curved phononic crystal waveguides, each having the shape of a circular arc. For example, a spiral shape may be formed by connecting curved waveguide portions in cascade, each being a circular arc (e.g., a quarter-circle, or a half-circle) of increasing radius of curvature. As another example, a serpentine shape may be formed by connecting three curved waveguide portions in cascade, each of the curved waveguide portions being a circular arc, as shown in FIG. 7.

Figure 8A:
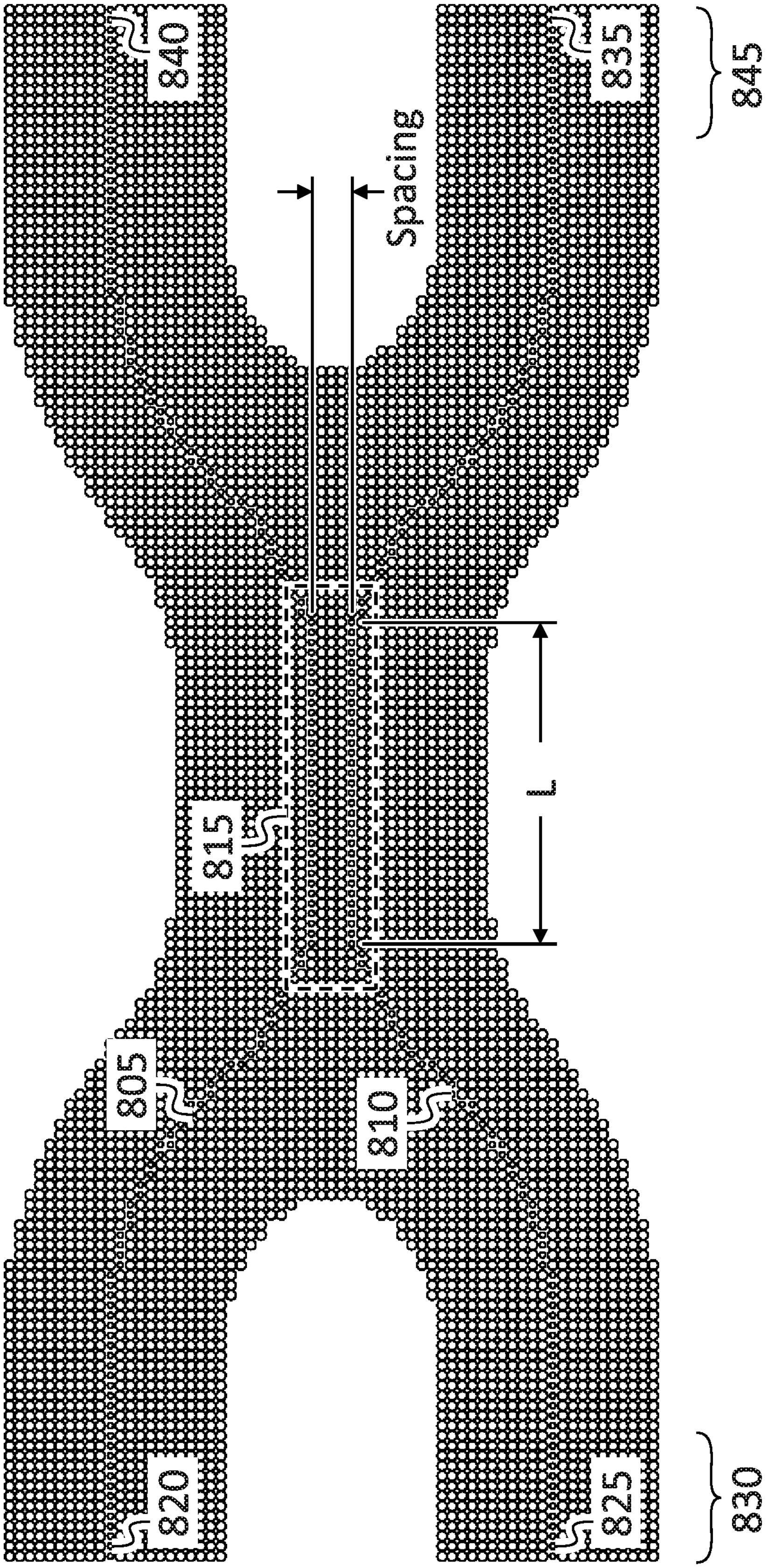
FIG. 8A is a top view of a phononic crystal coupler, according to an embodiment of the present disclosure.

In some embodiments, curved phononic crystal waveguides may be employed to fabricate a 2×2 coupler. Referring to FIG. 8A, in some embodiments, a two by two coupler may include a first waveguide 805 and a second waveguide 810, each of which extends through the coupler, and which interact with each other in an interaction region 815. The coupler may have a first port 820, and a second port 825 at a first end 830 of the coupler, and a third port 835, and a fourth port 840 at a second end 845 of the coupler. The first waveguide may connect the first port 820 and the fourth port 840, as shown in FIG. 8A, and the second waveguide may connect the second port 825 and the third port 835, as further shown in FIG. 8A. In the interaction region 815, the waveguides may be substantially parallel and separated by a spacing that is sufficiently small to allow acoustic energy, in the form of guided longitudinal sound waves propagating in one of the phononic crystal waveguides to be coupled into the other phononic crystal waveguide.

In some embodiments, the ports at one end of the phononic crystal coupler, e.g., the third port 835 and the fourth port 840 at the second end 845 of the phononic crystal coupler, may be employed as inputs (i.e., acoustic signals may be fed to them) and the ports at the other end, e.g., the first port 820 and the second port 825 at the first end 830 of the phononic crystal coupler, may be used as outputs, e.g., acoustic signals transmitted from them may be received by a transducer (e.g., a transducer for converting acoustic signals to electrical signals) or by another acoustic element. In such an embodiment, the acoustic signal levels at the output ports may depend on the acoustic signals at the input ports, and on the characteristics of the coupler, e.g., the length of the interaction region 815 (labelled L in FIG. 8A), and the spacing between the waveguides in the interaction region 815, as discussed in further detail below. The coupler may be a substantially linear device, so that, for example, if the third port 835 and the fourth port 840 receive a first acoustic input signal and a second acoustic input signal, respectively, the output signal at, e.g., the first port 820, may be a linear superposition of (i) an acoustic output signal that would be received at the first port if the first acoustic input signal were absent, and (ii) an acoustic output signal that would be received at the first port if the second acoustic input signal were absent.

In some embodiments, a coupler otherwise like that of FIG. 8A may have only three ports, with, for example, the end of the first waveguide that extends, in FIG. 8A, to the fourth port 840 being instead terminated just outside of the interaction region 815. In some embodiments the waveguides are not precisely straight and not precisely parallel within the interaction region 815, but are instead straight and parallel to within, e.g., 10 degrees within the interaction region 815.

The coupled waveguides in the interaction region of the phononic crystal coupler may support two eigenmodes for each direction of propagation (e.g., right to left in FIG. 8A, or left to right), an even mode (which is symmetric about a central plane, the central plane being parallel to both waveguides, perpendicular to the sheet, and positioned half-way between the waveguides) and an odd mode (which is anti-symmetric about the central plane). At an entrance plane perpendicular to the two waveguides at the beginning of the interaction region 815, any combination of amplitudes and phases of the waves in the two waveguides entering the interaction region 815 may be approximately (or substantially) equal to a linear combination of the even mode and the odd mode. For example, if an input signal is present at the third port 835, and no signal is present at the fourth port 840, then the signal entering the interaction region 815 may be proportional to the sum of the even mode and the odd mode. If instead an input signal is present at the fourth port 840, and no signal is present at the third port 835, then the signal entering the interaction region 815 may be proportional to the difference of the even mode and the odd mode.

The even mode and the odd mode may have different phase velocities. The difference in their phase velocities may increase as the spacing between the waveguides is reduced, and the phase velocity difference may also depend on the waveguide profile radius function of each of the waveguides, with a waveguide profile radius function that produces a less confined mode resulting in a greater phase velocity difference. As a result of the phase velocity difference, power may be transferred from one waveguide to the other (and back) as the sound waves travel along the interaction region 815. As mentioned above, reducing the spacing between the waveguides may cause the phase velocity difference to be increased, making possible a more compact coupler design for a given coupling factor. However, reducing the spacing between the waveguides may also result in mode shapes for the odd and even modes that that are less well matched to the eigenmode of a single waveguide, and return loss (and insertion loss) may degrade if the spacing between the waveguides is made too small.

The 2×2 coupler may be fabricated on a square grid as shown. This may, as mentioned above, make possible the fabrication of curved phononic crystal waveguides with relatively small radii of curvature (e.g., between 10 times the grid spacing and 1000 times the grid spacing). Although on a square grid it is also possible to fabricate a curved phononic crystal waveguide with a radius that is smaller than 10 times the grid spacing, a design that has very small radii of curvature may show a degradation of return loss, of insertion loss, and of isolation between ports at the same end of the coupler. The insertion loss may increase for small radii of curvature because the bandgap may be perturbed, inducing leakage.

For example, if the signal entering the interaction region 815 is proportional to the sum of the even mode and the odd mode (i.e., the two modes are in phase at the entrance of the interaction region 815, and all of the acoustic power is in the second waveguide), then after the acoustic signals have propagated sufficiently far (e.g., a first distance), along the interaction region 815 (assuming the interaction region 815 is sufficiently long), the phase velocity difference will cause the even mode and the odd mode to be out of phase instead of in phase, so that all of the acoustic power is in the first waveguide). If the acoustic signals travel far enough that the phase difference between the even mode and the odd mode increases further until it is 360 degrees (i.e., 2 pi), then the modes are in phase again and is one in which all of the acoustic power is again in the second waveguide.

At intermediate distances along the interaction region 815, the amount of coupling may have an intermediate value. For example, at a point that is half of the first distance from the entrance to the interaction region 815, the accumulated phase difference due to the phase velocity difference may be pi/2 (90 degrees) so that that if at the entrance to the interaction region 815 all of the power is in one waveguide, then at the point that is half of the first distance from the entrance to the interaction region 815, half of the acoustic power may be in each of the two waveguides.

Figure 8B:
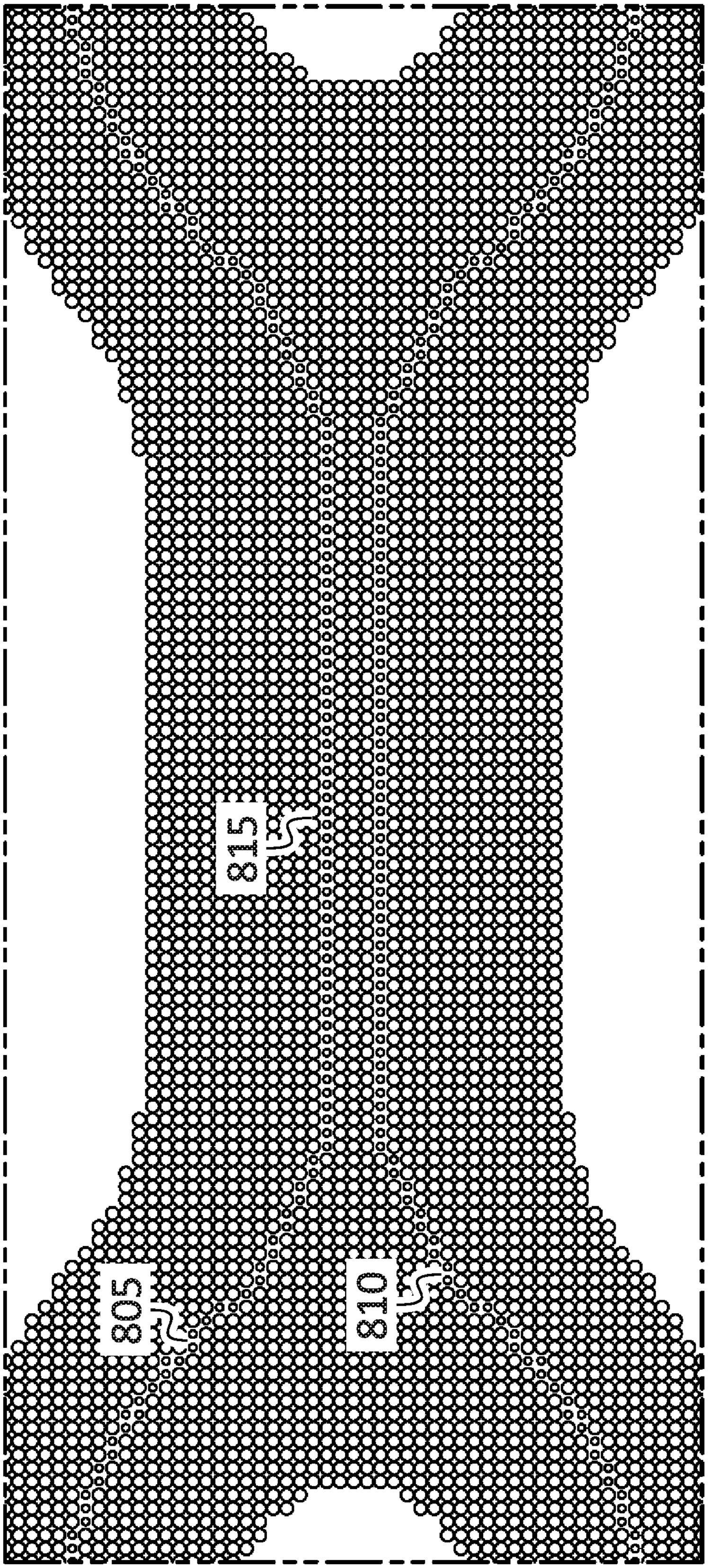
FIG. 8B is a top view of a portion of a phononic crystal coupler, according to an embodiment of the present disclosure.

For example, in the embodiment of FIG. 8B, the spacing between the waveguides in the interaction region 815 is four times the grid spacing, and the length of the interaction region 815 is 36 times the grid spacing. In this embodiment, when sound waves are received at the third port 835 and no sound waves are received at any other port, nearly all of the acoustic power (e.g., 99.6% of the acoustic power) is coupled to the first port 820, i.e., in the interaction region 815 most of the acoustic power is coupled from the second waveguide to the first waveguide. In FIG. 8B (and in FIGS. 8C and 8D), only a central portion of the coupler including the interaction region 815 is shown; the ports are not shown and may be substantially the same as those illustrated in FIG. 8A.

Figure 8C:
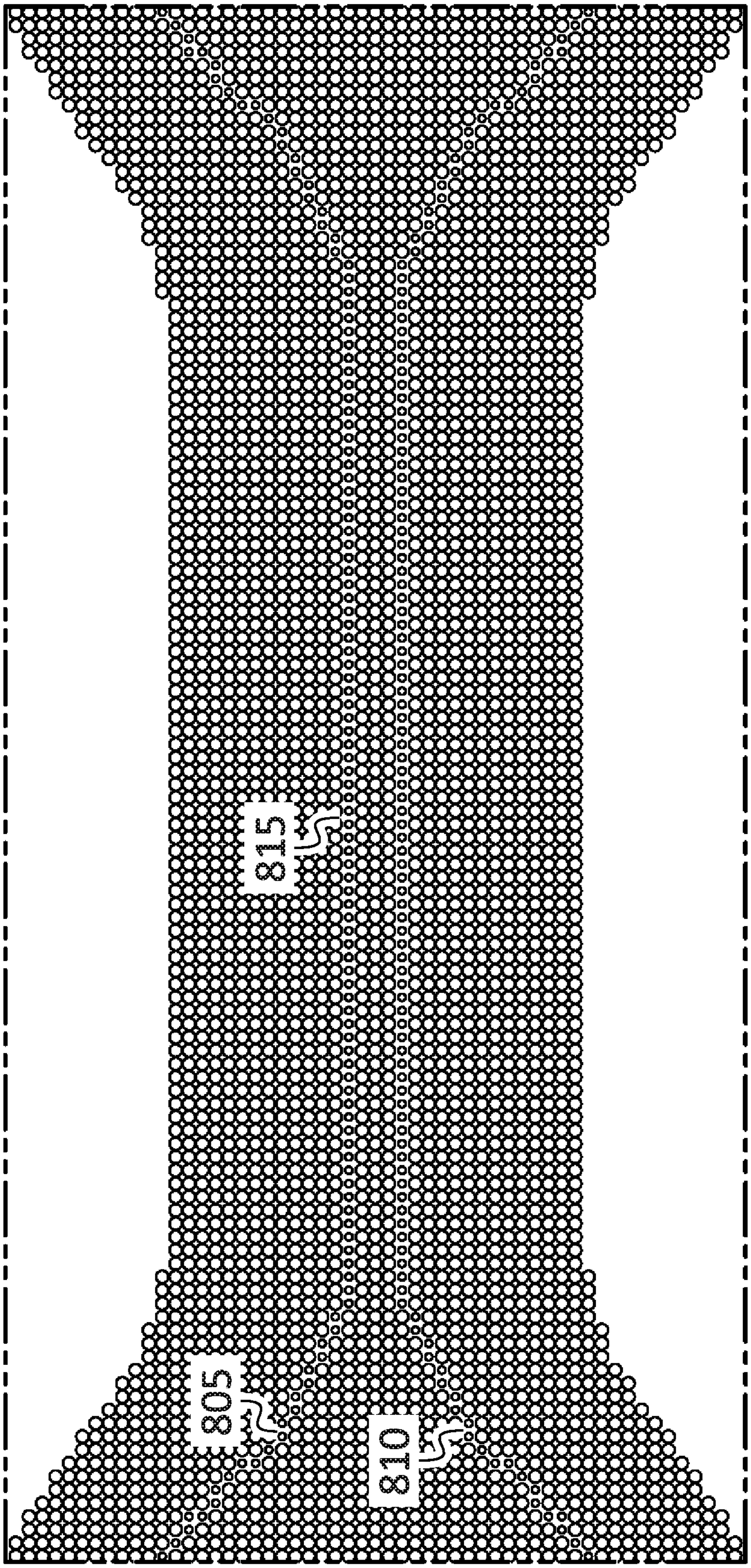
FIG. 8C is a top view of a portion of a phononic crystal coupler, according to an embodiment of the present disclosure.

In the embodiment of FIG. 8C, the spacing between the waveguides in the interaction region 815 is four times the grid spacing, and the length of the interaction region 815 is 60 times the grid spacing. In this embodiment, when sound waves are received at the third port 835 and no sound waves are received at any other port, half of the acoustic power is coupled to the first port 820. In the interaction region 815 most of the acoustic power is first coupled from the second waveguide to the first waveguide and then, further along the interaction region 815, half of the power is coupled back to the second waveguide.

Figure 8D:
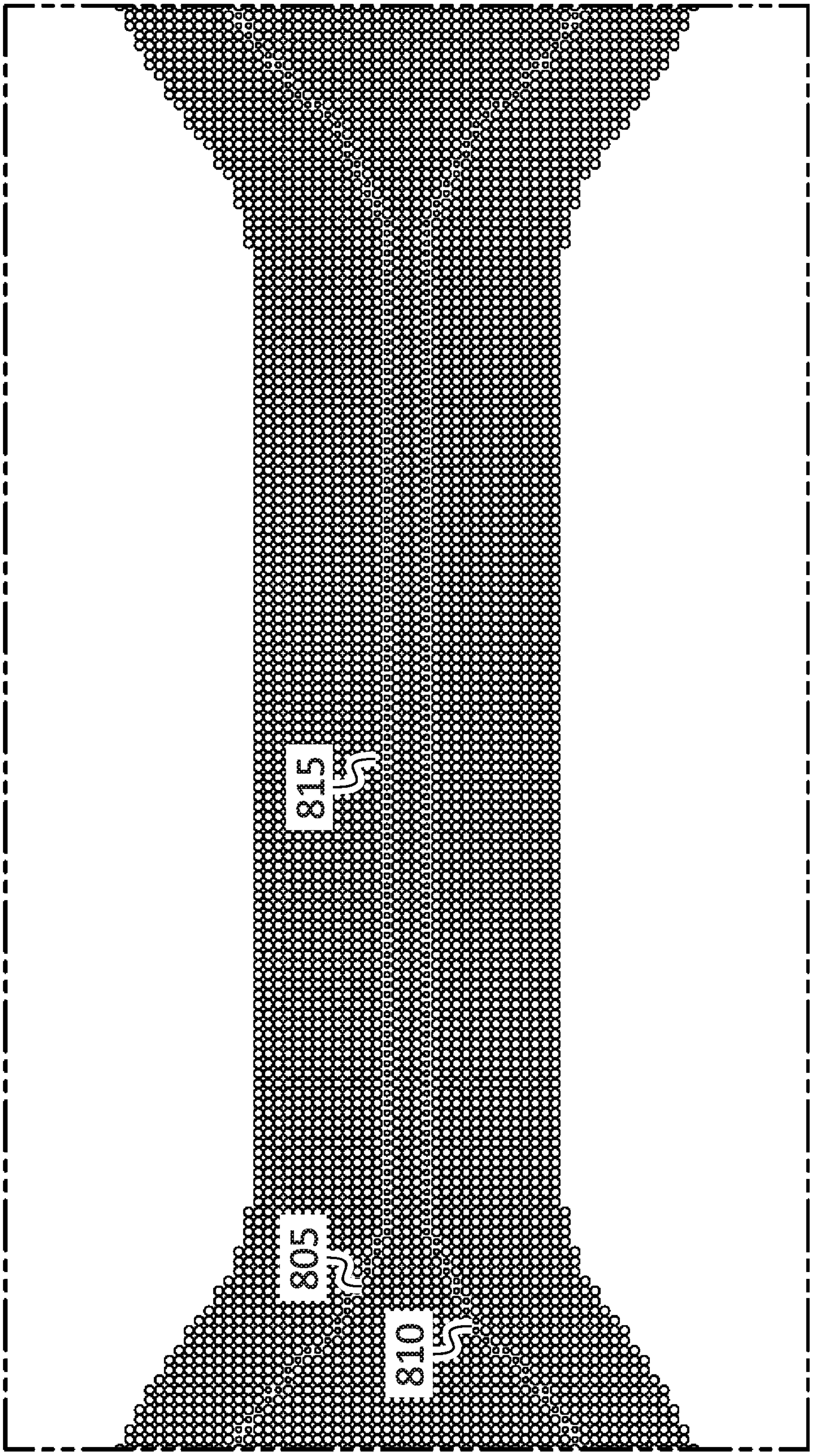
FIG. 8D is a top view of a portion of a phononic crystal coupler, according to an embodiment of the present disclosure.

In the embodiment of FIG. 8D, the spacing between the waveguides in the interaction region 815 is four times the grid spacing, and the length of the interaction region 815 is 84 times the grid spacing. In this embodiment, when sound waves are received at the third port 835 and no sound waves are received at any other port, nearly all of the acoustic power (e.g., 99.6% of the acoustic power) is coupled to the second port 825. In the interaction region 815, most of the acoustic power is coupled from the second waveguide to the first waveguide; and then, further along the interaction region 815, most of the power is coupled back to the second waveguide. In each of the above-described embodiments, no power or very little power is reflected to the fourth port 840.

Couplers, with coupling ratios near (or about) 50%, may be useful, for example, in constructing acoustic interferometers, such as an acoustic Mach-Zehnder interferometer or an acoustic Michelson interferometer. Couplers with small coupling ratios (e.g., less than 5%) may be useful, for example, for coupling power into or out of a resonator without significantly degrading the quality factor of the resonator, or for coupling power to a resonator in such a manner that the ratio of the power circulating in the resonator is as great as possible, or nearly as great as possible, for a given input power in the feed waveguide. As used herein, the "coupling ratio" is the fraction of the acoustic power received by the coupler at a port of one of the waveguides at one end of the coupler that is coupled to an port of the other waveguide, at the other end of the coupler.

Figure 9A:
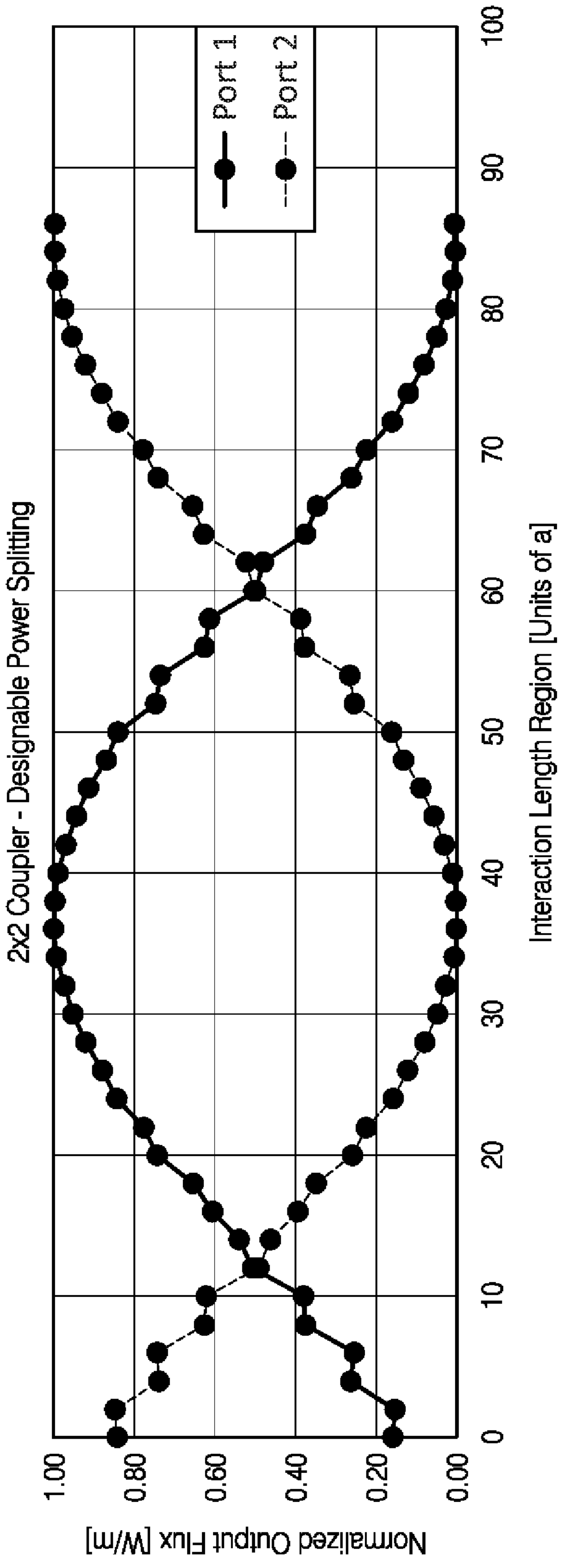
FIG. 9A is a graph of phononic crystal coupler characteristics, according to an embodiment of the present disclosure.

FIG. 9A is a graph of acoustic output power at the first port 820 and at the second port 825, when sound waves are received at the third port 835 and no sound waves are received at any other port, as a function of the length of the interaction region 815. It may be seen from this graph that in an embodiment like that of FIG. 8B, in which the spacing between the waveguides in the interaction region 815 is four times the grid spacing, and the length of the interaction region 815 is 13 times the grid spacing, it may be expected that when sound waves are received at the third port 835 and no sound waves are received at any other port, half of the acoustic power received at the third port 835 will be coupled to the first port 820. This result is also demonstrated by the graph of FIG. 9C, discussed in further detail below. It will be understood that the interaction region length may be defined in various ways, because waves in the two waveguides interact with increasing strength as the waveguides approach each other. For the purposes of the claims, the length of interaction region is defined as the length of the region within which the spacing between the waveguides is less than 1.5 times its minimum spacing.

Figure 9B:
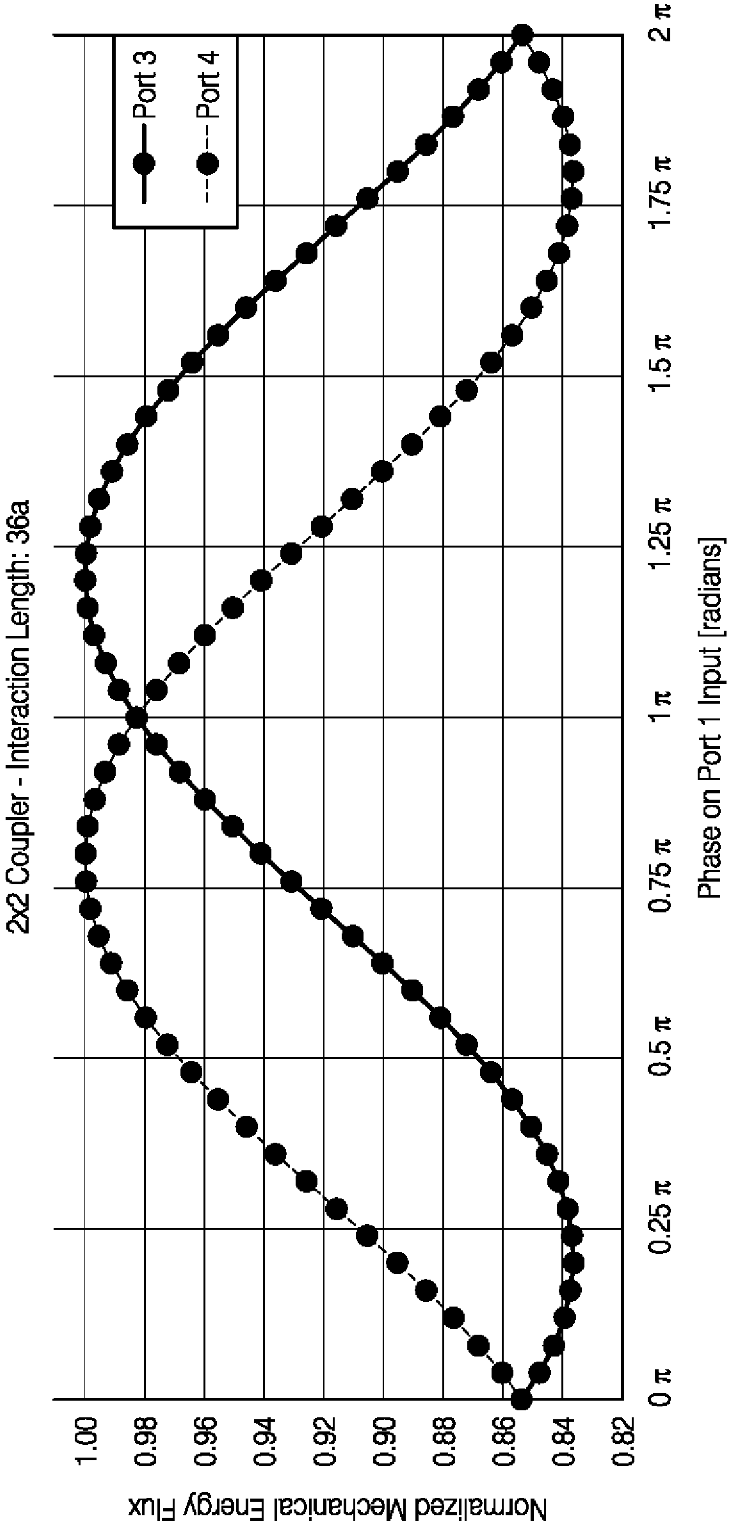
FIG. 9B is a graph of phononic crystal coupler characteristics, according to an embodiment of the present disclosure.
Figure 9C:
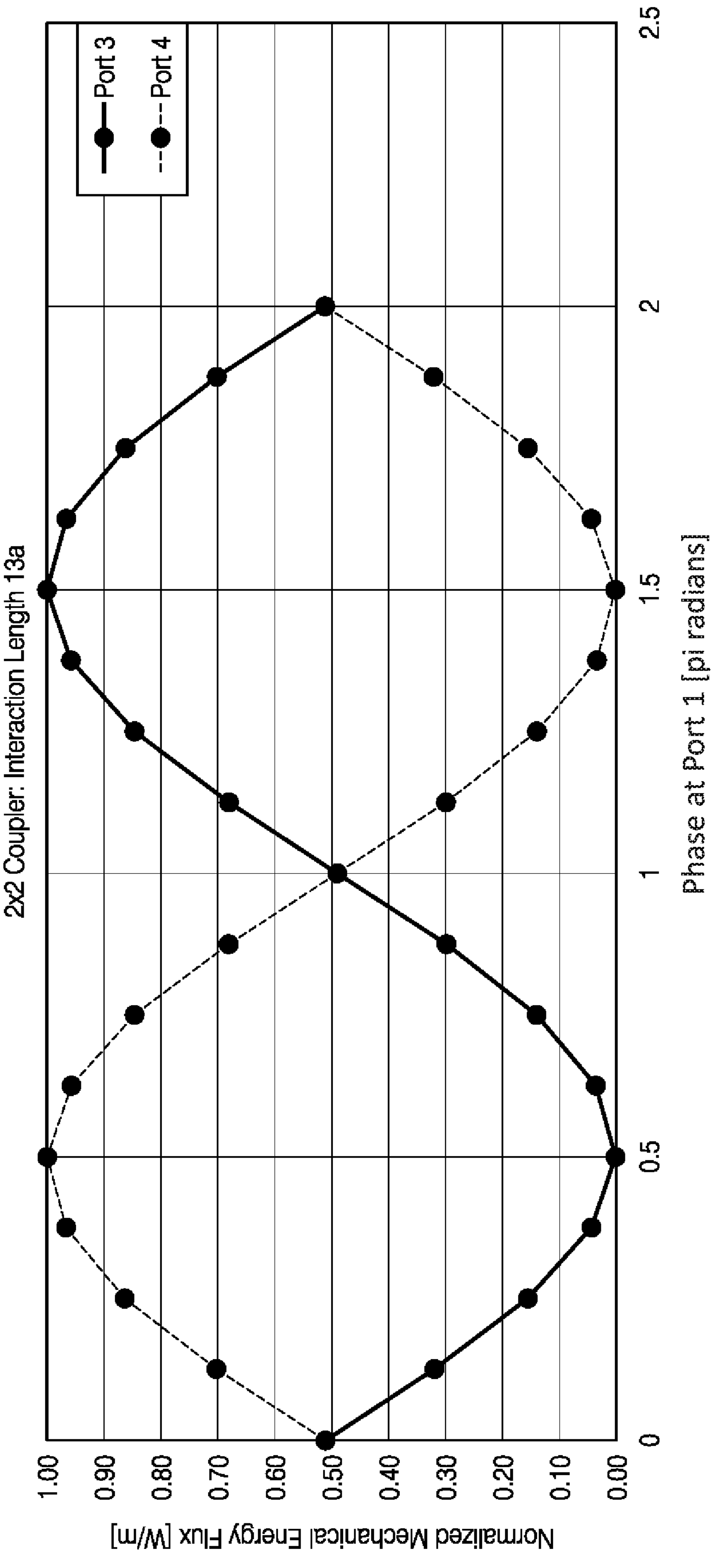
FIG. 9C is a graph of phononic crystal coupler characteristics, according to an embodiment of the present disclosure.

FIG. 9B is a graph of the normalized output power at the third port 835 and at the fourth port 840, for a coupler in which the length of the interaction region 815 is 36 times the grid spacing, as a function of the phase difference between two equal-amplitude input signals fed to the coupler at the first port 820 and at the second port 825. FIG. 9C is a graph of the normalized output power at the third port 835 and at the fourth port 840, for a coupler in which the length of the interaction region 815 is 13 times the grid spacing, as a function of the phase difference between two equal-amplitude input signals fed to the coupler at first port 820 and at the second port 825. As mentioned above, a coupler with an interaction region 815 of this length may have the property that when sound waves are received at one of the two ports at one end of the coupler, and no sound waves are received at any other port, half of the received power is coupled to each of the two ports at the other end of the coupler. It may be seen from FIG. 9C that at certain relative phase angles (e.g., pi/2 and 3 pi/2), the contributions, at one of the output ports, from the two input ports, cancel (or "interfere destructively"), causing that output port to receive substantially none of the acoustic power fed into the coupler.

In view of the foregoing, a phononic crystal coupler may be constructed from two phononic crystal waveguides that are curved so that they are near each other in an interaction region. The design parameters of such coupler include the spacing between the waveguides in the interaction region and the length of the interaction region; couplers with various suitable coupling ratios may be constructed by varying these design parameters.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed herein could be termed a second element, component, region, layer or section, without departing from the spirit and scope of the inventive concept.

Spatially relative terms, such as "beneath", "below", "lower", "under", "above", "upper" and the like, may be used herein for ease of description to describe one element or feature's relationship to another element(s) or feature(s) as illustrated in the figures. It will be understood that such spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the inventive concept. As used herein, the terms "substantially," "about," and similar terms are used as terms of approximation and not as terms of degree, and are intended to account for the inherent deviations in measured or calculated values that would be recognized by those of ordinary skill in the art. As used herein, the term "major component" refers to a component that is present in a composition, polymer, or product in an amount greater than an amount of any other single component in the composition or product. In contrast, the term "primary component" refers to a component that makes up at least 50% by weight or more of the composition, polymer, or product. As used herein, the term "major portion", when applied to a plurality of items, means at least half of the items.

As used herein, the singular forms "a" and "an" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the inventive concept refers to "one or more embodiments of the present disclosure". Also, the term "exemplary" is intended to refer to an example or illustration.

As used herein, the terms "use," "using," and "used" may be considered synonymous with the terms "utilize," "utilizing," and "utilized," respectively.

It will be understood that when an element or layer is referred to as being "on", "connected to", "coupled to", or "adjacent to" another element or layer, it may be directly on, connected to, coupled to, or adjacent to the other element or layer, or one or more intervening elements or layers may be present. In contrast, when an element or layer is referred to as being "directly on", "directly connected to", "directly coupled to", or "immediately adjacent to" another element or layer, there are no intervening elements or layers present.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein.

Although exemplary embodiments of a phononic crystal coupler have been specifically described and illustrated herein, many modifications and variations will be apparent to those skilled in the art. Accordingly, it is to be understood that a phononic crystal coupler constructed according to principles of this disclosure may be embodied other than as specifically described herein. The invention is also defined in the following claims, and equivalents thereof.

What is claimed is:

1. A phononic coupler, comprising:
- a sheet, including a plurality of standard reflectors, and
- a plurality of divergent reflectors defining, among the standard reflectors:
  - a first waveguide, and
  - a second waveguide,
- the phononic coupler having:
  - a first port, at a first end of the phononic coupler,
  - a second port, at the first end of the phononic coupler, and
  - a third port, at a second end of the phononic coupler,
- the first waveguide having a first end at the first port,
- the second waveguide having:
  - a first end at the second port, and
  - a second end at the third port,
- the phononic coupler being configured to couple sound waves, at a frequency greater than 10 MHz and less than 100 GHz, received at the third port, to both the first port and the second port, at least 0.1% of the received sound wave power being coupled to the first port, and at least 0.1% of the received sound wave power being coupled to the second port.

2. The phononic coupler of claim 1, wherein:
- the sheet is composed of a material having a bulk propagation loss, for sound waves at a frequency greater than 10 MHz and less than 100 GHz, of less than 1 dB/micron,
- the sheet includes:
  - a plurality of standard reflectors, each of the standard reflectors being associated with a respective grid point of a grid defined by a plurality of intersecting lines, each grid point being a respective intersection of two lines of the plurality of intersecting lines, the grid being locally periodic to within 5%, and having a local grid spacing, each of the standard reflectors having a center separated from the respective grid point of the standard reflector by at most 1% of the grid spacing, and
  - a plurality of divergent reflectors, each associated with a respective grid point, the divergent reflectors defining a waveguide among the standard reflectors, each of the divergent reflectors being an absent reflector or a reflector that is smaller than one of the standard reflectors.

3. The phononic coupler of claim 2, wherein, within an interaction region of the phononic coupler:
- the grid spacing is constant to within 5%; and
- the second waveguide is:
  - parallel, to within 10 degrees, to the first waveguide, and
  - separated from the first waveguide by at most 10 times a maximum grid spacing in the interaction region.

4. The phononic coupler of claim 3, wherein, within the interaction region, the second waveguide is separated from the first waveguide by at most 5 times a maximum grid spacing in the interaction region.

5. The phononic coupler of claim 3, wherein the interaction region has a length of at least 10 times the maximum grid spacing.

6. The phononic coupler of claim 3, wherein the interaction region has a length of at least 30 times the maximum grid spacing.

7. The phononic coupler of claim 3, wherein the interaction region has a length of at least 60 times the maximum grid spacing.

8. The phononic coupler of claim 3, wherein the first waveguide has a curved portion outside of the interaction region, the waveguide having, at a first point within the curved portion, a centerline with a radius of curvature, at the first point along the waveguide, of less than 1,000 times a minimum separation between adjacent reflectors of the plurality of standard reflectors.

9. The phononic coupler of claim 8, wherein:

the grid is defined by:

a first plurality of parallel, straight lines, and a second plurality of parallel, straight lines, successive lines of the first plurality of parallel, straight lines are separated by the grid spacing at the first point, and successive lines of the second plurality of parallel, straight lines are separated by the grid spacing at the first point.

10. The phononic coupler of claim 8, wherein:

each of the standard reflectors is a hole in the sheet having a radius differing from a standard hole radius by at most 5% each of the divergent reflectors is separated from the centerline of the waveguide by a transverse offset distance, each of the divergent reflectors is:

a hole having a reduced radius smaller than the standard hole radius, the reduced radius differing by at most 5% from a radius determined by a waveguide profile radius function evaluated at the transverse offset distance, or an absence of a reflector.

11. The phononic coupler of claim 10, wherein each of the divergent reflectors is:

a hole, when the waveguide profile radius function evaluated at the transverse offset distance exceeds a threshold radius value, and an absence of a reflector otherwise.

12. The phononic coupler of claim 11, wherein the waveguide profile radius function is a piecewise constant function.

13. The phononic coupler of claim 12, wherein the waveguide profile radius function returns a first value when the transverse offset distance is less than a threshold offset distance, the threshold offset distance being less than the grid spacing at the first point.

14. The phononic coupler of claim 10, wherein the waveguide profile radius function is a Lorentzian function.

15. The phononic coupler of claim 10, wherein the waveguide profile radius function is function that is everywhere piecewise Lorentzian or piecewise constant.

16. The phononic coupler of claim 1, further comprising a fourth port, at the second end of the phononic coupler, the first waveguide having a second end at the fourth port.

17. The phononic coupler of claim 16, wherein an acoustic output signal at the first port, in response to:

a first acoustic input signal received at the third port and a second acoustic input signal received at the fourth port is a linear superposition of:

an acoustic output signal that would be received at the first port if the first acoustic input signal were absent, and an acoustic output signal that would be received at the first port if the second acoustic input signal were absent.

18. The phononic coupler of claim 1, wherein the phononic coupler has a coupling ratio of between 45% and 55%.

19. The phononic coupler of claim 1, wherein the phononic coupler has a coupling ratio of between 70% and 90%.

20. The phononic coupler of claim 1, wherein the phononic coupler has a coupling ratio of between 0.1% and 5%.

21. The phononic coupler of claim 1, wherein the sound waves are waves of a kind selected from the group consisting of longitudinal waves, surface waves, Lamb waves, Love waves, Stoneley waves, Sezawa waves, and combinations thereof.

* * * * *